United States Patent
Lee et al.

(10) Patent No.: US 10,793,628 B2
(45) Date of Patent: Oct. 6, 2020

(54) ISOLATED ANTIBODIES AGAINST INTERLEUKIN-17 RECEPTOR B (IL-17RB) FOR CANCER THERAPY

(71) Applicant: Academia Sinica, Taipei (TW)

(72) Inventors: Wen-Hwa Lee, Taipei (TW); Jin-Yuh Shew, Taipei (TW); Che Ma, Taipei (TW); Chia-Lin Chen, Taipei (TW); Wen-Hsin Lee, Taipei (TW); Chun-Kai Huang, Taipei (TW); Heng-Hsiung Wu, Taipei (TW)

(73) Assignee: Academia Sinica, Taipei (TW)

( * ) Notice: Subject to any disclaimer, the term of this patent is extended or adjusted under 35 U.S.C. 154(b) by 8 days.

(21) Appl. No.: 15/322,788

(22) PCT Filed: Jun. 30, 2015

(86) PCT No.: PCT/US2015/038565
§ 371 (c)(1),
(2) Date: Dec. 29, 2016

(87) PCT Pub. No.: WO2016/004045
PCT Pub. Date: Jan. 7, 2016

(65) Prior Publication Data
US 2018/0201672 A1   Jul. 19, 2018

Related U.S. Application Data

(60) Provisional application No. 62/019,421, filed on Jun. 30, 2014.

(51) Int. Cl.
| A61K 39/395 | (2006.01) |
| C07K 16/24  | (2006.01) |
| A61K 45/06  | (2006.01) |
| A61K 31/713 | (2006.01) |
| A61K 38/20  | (2006.01) |
| C07K 16/28  | (2006.01) |
| C07K 16/30  | (2006.01) |
| A61P 35/00  | (2006.01) |
| C07K 14/715 | (2006.01) |
| C12N 15/113 | (2010.01) |
| A61K 39/00  | (2006.01) |

(52) U.S. Cl.
CPC .......... *C07K 16/244* (2013.01); *A61K 31/713* (2013.01); *A61K 38/20* (2013.01); *A61K 39/39558* (2013.01); *A61K 45/06* (2013.01); *A61P 35/00* (2018.01); *C07K 14/7155* (2013.01); *C07K 16/2866* (2013.01); *C07K 16/30* (2013.01); *C12N 15/1136* (2013.01); *A61K 2039/505* (2013.01); *C07K 2317/24* (2013.01); *C07K 2317/56* (2013.01); *C07K 2317/565* (2013.01); *C07K 2317/73* (2013.01); *C07K 2317/76* (2013.01); *C12N 2310/14* (2013.01); *C12N 2320/31* (2013.01)

(58) Field of Classification Search
None
See application file for complete search history.

(56) References Cited

U.S. PATENT DOCUMENTS

| 6,309,636 | B1 * | 10/2001 | do Couto | A61K 51/1051 424/133.1 |
| 6,849,719 | B2 * | 2/2005 | Shi | C07K 14/54 435/69.7 |
| 2002/0042089 | A1 | 4/2002 | Bodmer et al. | |
| 2003/0092881 | A1 | 5/2003 | Gorman | |
| 2009/0291097 | A1 * | 11/2009 | Chen | C07K 14/54 424/185.1 |
| 2013/0028835 | A1 | 1/2013 | Goetsch et al. | |
| 2013/0122015 | A1 | 5/2013 | Getts et al. | |
| 2013/0312126 | A1 | 11/2013 | Kay et al. | |

FOREIGN PATENT DOCUMENTS

WO   WO 2013/186236 A1   12/2013

OTHER PUBLICATIONS

Genbank Submission; NIH/NCBI, Accession NM_014443. Homo sapiens interleukin 17B (IL17B) mRNA; Feb. 9, 2014; pp. 1-3.
Huang et al., Autocrine/paracrine mechanism of interleukin-17B receptor promotes breast tumorigenesis through NF-κB-mediated antiapoptotic pathway. Oncogene. Jun. 5, 2014;33(23):2968-77. doi: 10.1038/onc.2013.268. Epub Jul. 15, 2013.
Lucas et al., UniProt KB Accession G8QSE5; Transcriptional regular, Spirochaeta. Feb. 22, 2012; pp. 1-2.

\* cited by examiner

*Primary Examiner* — Dong Jiang
(74) *Attorney, Agent, or Firm* — Wolf, Greenfield & Sacks, P.C.

(57) ABSTRACT

Methods and compositions for treatment and therapy of cancer are provided. Specifically, antagonists specific for interleukin-17 receptor B (IL-17RB) and its ligand IL-17B are provided. Potent neutralizing antibodies specific for IL-17RB and methods for their manufacture and use are disclosed. The invention also relates to antisense, RNAi and shRNA compositions for the prevention and treatment of cancer, in particular breast cancer and pancreatic cancer.

14 Claims, 10 Drawing Sheets
Specification includes a Sequence Listing.

A.

B.

C.

| Variables | Univariate HR (95% CI) | p | Multivariate HR (95% CI) | p |
|---|---|---|---|---|
| IL17RB positive stain (vs. negative group) | 1.97 (1.10-3.50) | 0.02 | 2.08 (1.09-3.97) | 0.03 |
| Age (≥ 50 years old)* | 0.67 (0.39-1.17) | 0.16 | 0.73 (0.38-1.41) | 0.35 |
| Tumor size (per cm) | 1.13 (1.06-1.21) | 0.0002 | 1.20 (1.06-1.36) | 0.004 |
| Lymph-node positive (vs. negative group) | 2.58 (1.21-5.53) | 0.015 | 4.36 (1.69-11.31) | 0.003 |
| Estrogen-receptor positive stain (vs. negative group) | 0.47 (0.27-0.82) | 0.008 | 0.28 (0.15-0.54) | 0.0002 |

*Median age: 50 years old, HR: hazard ratio, CI: confidence interval

A

B

A

B

SEQUENCE LISTING

```
<160> NUMBER OF SEQ ID NOS: 19

<210> SEQ ID NO 1
<211> LENGTH: 502
<212> TYPE: PRT
<213> ORGANISM: Homo sapiens

<400> SEQUENCE: 1

Met Ser Leu Val Leu Leu Ser Leu Ala Ala Leu Cys Arg Ser Ala Val
1               5                   10                  15

Pro Arg Glu Pro Thr Val Gln Cys Gly Ser Glu Thr Gly Pro Ser Pro
            20                  25                  30

Glu Trp Met Leu Gln His Asp Leu Ile Pro Gly Asp Leu Arg Asp Leu
        35                  40                  45

Arg Val Glu Pro Val Thr Thr Ser Val Ala Thr Gly Asp Tyr Ser Ile
    50                  55                  60

Leu Met Asn Val Ser Trp Val Leu Arg Ala Asp Ala Ser Ile Arg Leu
65                  70                  75                  80

Leu Lys Ala Thr Lys Ile Cys Val Thr Gly Lys Ser Asn Phe Gln Ser
                85                  90                  95

Tyr Ser Cys Val Arg Cys Asn Tyr Thr Glu Ala Phe Gln Thr Gln Thr
            100                 105                 110

Arg Pro Ser Gly Gly Lys Trp Thr Phe Ser Tyr Ile Gly Phe Pro Val
        115                 120                 125

Glu Leu Asn Thr Val Tyr Phe Ile Gly Ala His Asn Ile Pro Asn Ala
    130                 135                 140

Asn Met Asn Glu Asp Gly Pro Ser Met Ser Val Asn Phe Thr Ser Pro
145                 150                 155                 160
```

| | | | | | | | | | | | | |
|---|---|---|---|---|---|---|---|---|---|---|---|---|
|Gly|Cys|Leu|Asp|His|Ile|Met|Lys|Tyr|Lys|Lys|Cys|Val|Lys|Ala|
| | | |  |165|   |   |   |170|   |   |   |175|   |   |

Gly Cys Leu Asp His Ile Met Lys Tyr Lys Lys Cys Val Lys Ala
                     165               170               175

Gly Ser Leu Trp Asp Pro Asn Ile Thr Ala Cys Lys Lys Asn Glu Glu
            180               185               190

Thr Val Glu Val Asn Phe Thr Thr Thr Pro Leu Gly Asn Arg Tyr Met
        195               200              205

Ala Leu Ile Gln His Ser Thr Ile Ile Gly Phe Ser Gln Val Phe Glu
      210               215              220

Pro His Gln Lys Lys Gln Thr Arg Ala Ser Val Ile Pro Val Thr
225             230              235           240

Gly Asp Ser Glu Gly Ala Thr Val Gln Leu Thr Pro Tyr Phe Pro Thr
            245             250             255

Cys Gly Ser Asp Cys Ile Arg His Lys Gly Thr Val Val Leu Cys Pro
        260               265             270

Gln Thr Gly Val Pro Phe Pro Leu Asp Asn Asn Lys Ser Lys Pro Gly
      275               280              285

Gly Trp Leu Pro Leu Leu Leu Ser Leu Leu Val Ala Thr Trp Val
    290              295               300

Leu Val Ala Gly Ile Tyr Leu Met Trp Arg His Glu Arg Ile Lys Lys
305             310             315           320

Thr Ser Phe Ser Thr Thr Thr Leu Leu Pro Pro Ile Lys Val Leu Val
            325             330             335

Val Tyr Pro Ser Glu Ile Cys Phe His His Thr Ile Cys Tyr Phe Thr
        340               345             350

Glu Phe Leu Gln Asn His Cys Arg Ser Glu Val Ile Leu Glu Lys Trp
      355               360              365

Gln Lys Lys Lys Ile Ala Glu Met Gly Pro Val Gln Trp Leu Ala Thr
370             375             380

Gln Lys Lys Ala Ala Asp Lys Val Val Phe Leu Leu Ser Asn Asp Val
385            390              395           400

Asn Ser Val Cys Asp Gly Thr Cys Gly Lys Ser Glu Gly Ser Pro Ser
            405             410             415

Glu Asn Ser Gln Asp Leu Phe Pro Leu Ala Phe Asn Leu Phe Cys Ser
      420               425              430

Asp Leu Arg Ser Gln Ile His Leu His Lys Tyr Val Val Tyr Phe
        435               440              445

Arg Glu Ile Asp Thr Lys Asp Asp Tyr Asn Ala Leu Ser Val Cys Pro
450             455             460

Lys Tyr His Leu Met Lys Asp Ala Thr Ala Phe Cys Ala Glu Leu Leu
465            470              475           480

His Val Lys Gln Gln Val Ser Ala Gly Lys Arg Ser Gln Ala Cys His
            485             490             495

Asp Gly Cys Cys Ser Leu
      500

<210> SEQ ID NO 2
<211> LENGTH: 1509
<212> TYPE: DNA
<213> ORGANISM: Homo sapiens

<400> SEQUENCE: 2
atgtcgctcg tgctgctaag cctggccgcg ctgtgcagga gcgccgtacc ccgagagccg    60
accgttcaat gtggctctga aactgggcca tctccagagt ggatgctaca acatgatcta   120

```
atccccggag acttgaggga cctccgagta gaacctgtta caactagtgt tgcaacaggg    180
gactattcaa ttttgatgaa tgtaagctgg gtactccggg cagatgccag catccgcttg    240
ttgaaggcca ccaagatttg tgtgacgggc aaaagcaact tccagtccta cagctgtgtg    300
aggtgcaatt acacagaggc cttccagact cagaccagac cctctggtgg taaatggaca    360
ttttcctaca tcggcttccc tgtagagctg aacacagtct atttcattgg ggcccataat    420
attcctaatg caaatatgaa tgaagatggc ccttccatgt ctgtgaattt cacctcacca    480
ggctgcctag accacataat gaaatataaa aaaagtgtg tcaaggccgg aagcctgtgg     540
gatccgaaca tcactgcttg taagaagaat gaggagacag tagaagtgaa cttcacaacc    600
actcccctgg gaaacagata catggctctt atccaacaca gcactatcat cgggttttct    660
caggtgtttg agccacacca gaagaaacaa acgcgagctt cagtggtgat tccagtgact    720
ggggatagtg aaggtgctac ggtgcagctg actccatatt ttcctacttg tggcagcgac    780
tgcatccgac ataaaggaac agttgtgctc tgcccacaaa caggcgtccc tttccctctg    840
gataacaaca aaagcaagcc gggaggctgg ctgcctctcc tcctgctgtc tctgctggtg    900
gccacatggg tgctggtggc agggatctat ctaatgtgga ggcacgaaag gatcaagaag    960
acttcctttt ctaccaccac actactgccc cccattaagg ttcttgtggt ttacccatct   1020
gaaatatgtt tccatcacac aatttgttac ttcactgaat ttcttcaaaa ccattgcaga   1080
agtgaggtca tccttgaaaa gtggcagaaa aagaaaatag cagagatggg tccagtgcag   1140
tggcttgcca ctcaaaagaa ggcagcagac aaagtcgtct tccttctttc caatgacgtc   1200
aacagtgtgt gcgatggtac ctgtggcaag agcgagggca gtcccagtga aactctcaa    1260
gacctcttcc cccttgcctt taaccttttc tgcagtgatc taagaagcca gattcatctg   1320
cacaaatacg tggtggtcta ctttagagag attgatacaa aagacgatta caatgctctc   1380
agtgtctgcc ccaagtacca cctcatgaag gatgccactg ctttctgtgc agaacttctc   1440
catgtcaagc agcaggtgtc agcaggaaaa agatcacaag cctgccacga tggctgctgc   1500
tccttgtag                                                           1509
```

<210> SEQ ID NO 3  
<211> LENGTH: 180  
<212> TYPE: PRT  
<213> ORGANISM: Homo sapiens

<400> SEQUENCE: 3

```
Met Asp Trp Pro His Asn Leu Leu Phe Leu Leu Thr Ile Ser Ile Phe
1               5                   10                  15

Leu Gly Leu Gly Gln Pro Arg Ser Pro Lys Ser Lys Arg Lys Gly Gln
            20                  25                  30

Gly Arg Pro Gly Pro Leu Ala Pro Gly Pro His Gln Val Pro Leu Asp
        35                  40                  45

Leu Val Ser Arg Met Lys Pro Tyr Ala Arg Met Glu Glu Tyr Glu Arg
    50                  55                  60

Asn Ile Glu Glu Met Val Ala Gln Leu Arg Asn Ser Ser Glu Leu Ala
65                  70                  75                  80

Gln Arg Lys Cys Glu Val Asn Leu Gln Leu Trp Met Ser Asn Lys Arg
                85                  90                  95

Ser Leu Ser Pro Trp Gly Tyr Ser Ile Asn His Asp Pro Ser Arg Ile
            100                 105                 110

Pro Val Asp Leu Pro Glu Ala Arg Cys Leu Cys Leu Gly Cys Val Asn
        115                 120                 125
```

```
Pro Phe Thr Met Gln Glu Asp Arg Ser Met Val Ser Val Pro Val Phe
    130                 135                 140

Ser Gln Val Pro Val Arg Arg Leu Cys Pro Pro Pro Arg Thr
145                 150                 155                 160

Gly Pro Cys Arg Gln Arg Ala Val Met Glu Thr Ile Ala Val Gly Cys
                165                 170                 175

Thr Cys Ile Phe
            180

<210> SEQ ID NO 4
<211> LENGTH: 543
<212> TYPE: DNA
<213> ORGANISM: Homo sapiens

<400> SEQUENCE: 4
atggactggc ctcacaacct gctgtttctt cttaccattt ccatcttcct ggggctgggc      60
cagcccagga gccccaaaag caagaggaag gggcaagggc ggcctgggcc cctggccccct    120 ggccctcacc aggtgccact ggacctggtg tcacggatga aaccgtatgc ccgcatggag    180
gagtatgaga ggaacatcga ggagatggtg gcccagctga ggaacagctc agagctggcc    240
cagagaaagt gtgaggtcaa cttgcagctg tggatgtcca acaagaggag cctgtctccc    300
tggggctaca gcatcaacca cgaccccagc cgtatccccg tggacctgcc ggaggcacgg    360
tgcctgtgtc tgggctgtgt gaacccttc accatgcagg aggaccgcag catggtgagc    420
gtgccggtgt tcagccaggt tcctgtgcgc cgccgcctct gcccgccacc gccccgcaca    480
gggccttgcc gccagcgcgc agtcatggag accatcgctg tgggctgcac ctgcatcttc    540
tga                                                                  543

<210> SEQ ID NO 5
<211> LENGTH: 21
<212> TYPE: DNA
<213> ORGANISM: artificial sequence
<220> FEATURE:
<223> OTHER INFORMATION: shRNA

<400> SEQUENCE: 5
ccattaaggt tcttgtggtt t                                              21

<210> SEQ ID NO 6
<211> LENGTH: 21
<212> TYPE: DNA
<213> ORGANISM: Artificial Sequence
<220> FEATURE:
<223> OTHER INFORMATION: shRNA

<400> SEQUENCE: 6
ccatcacaca atttgttact t                                              21

<210> SEQ ID NO 7
<211> LENGTH: 21
<212> TYPE: DNA
<213> ORGANISM: Artificial Sequence
<220> FEATURE:
<223> OTHER INFORMATION: shRNA

<400> SEQUENCE: 7
cccataatat tcctaatgca a                                              21

<210> SEQ ID NO 8
```

```
<211> LENGTH: 21
<212> TYPE: DNA
<213> ORGANISM: Artificial Sequence
<220> FEATURE:
<223> OTHER INFORMATION: shRNA

<400> SEQUENCE: 8
gcagctgtgg atgtccaaca a                                              21

<210> SEQ ID NO 9
<211> LENGTH: 21
<212> TYPE: DNA
<213> ORGANISM: Artificial Sequence
<220> FEATURE:
<223> OTHER INFORMATION: shRNA

<400> SEQUENCE: 9
tcttaccatt tccatcttcc t                                              21

<210> SEQ ID NO 10
<211> LENGTH: 348
<212> TYPE: DNA
<213> ORGANISM: Artificial Sequence
<220> FEATURE:
<223> OTHER INFORMATION: VH nucleotide sequence

<400> SEQUENCE: 10
gaggttcagc tgcagcagtc tggacctgag ctggtgaagc ctggggcttc agtgaagata    60
tcctgcaaga cttctggata caccttcact gaatacacca tccactgggt gaagcagaac   120
catggaaaga gccttgactg gattggaggt attaatccta acaatggtgg tactacttac   180
aaccaggagt tcaagggcaa ggccacattg actgtagata agtcctccag tacagcctac   240
atggaattcc gcagcctgac atctgaggat tctgcagtct attactgtgc aagaagttac   300
tacggctacg tagactactg gggccaaggc accactctca ccgcggcc              348

<210> SEQ ID NO 11
<211> LENGTH: 318
<212> TYPE: DNA
<213> ORGANISM: Artificial Sequence
<220> FEATURE:
<223> OTHER INFORMATION: VL nucleotide sequence

<400> SEQUENCE: 11
caaattgttc tcacccagtc tccagcaatc atgtctgcat ctccagggga gaaggtcacc    60
atgacctgca gtgccagctc aagtatatat tacatacact ggtaccagca gaagtcaggc   120
acctccccca aaagatggat ttatgacaca tccaagctgg cttctggagt ccctgctcgc   180
ttcagtggca gtgggtctgg gacctcttac tctctcacaa tcagcagcat ggaggctgaa   240
gatgctgcca cttattactg ccagcagtgg agtagtaacc cattcacgtt cggctcgggg   300
acaaaattgg aaataaaa                                                 318

<210> SEQ ID NO 12
<211> LENGTH: 116
<212> TYPE: PRT
<213> ORGANISM: Artificial Sequence
<220> FEATURE:
<223> OTHER INFORMATION: VH amino acid sequence

<400> SEQUENCE: 12

Glu Val Gln Leu Gln Gln Ser Gly Pro Glu Leu Val Lys Pro Gly Ala
1               5                   10                  15
```

```
Ser Val Lys Ile Ser Cys Lys Thr Ser Gly Tyr Thr Phe Thr Glu Tyr
            20                  25                  30

Thr Ile His Trp Val Lys Gln Asn His Gly Lys Ser Leu Asp Trp Ile
        35                  40                  45

Gly Gly Ile Asn Pro Asn Asn Gly Gly Thr Thr Tyr Asn Gln Glu Phe
    50                  55                  60

Lys Gly Lys Ala Thr Leu Thr Val Asp Lys Ser Ser Ser Thr Ala Tyr
65                  70                  75                  80

Met Glu Phe Arg Ser Leu Thr Ser Glu Asp Ser Ala Val Tyr Tyr Cys
                85                  90                  95

Ala Arg Ser Tyr Tyr Gly Tyr Val Asp Tyr Trp Gly Gln Gly Thr Thr
            100                 105                 110

Leu Thr Ala Ala
        115
```

```
<210> SEQ ID NO 13
<211> LENGTH: 106
<212> TYPE: PRT
<213> ORGANISM: Artificial Sequence
<220> FEATURE:
<223> OTHER INFORMATION: VL amino acid sequence

<400> SEQUENCE: 13

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Tyr Tyr Ile
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Lys
            100                 105
```

```
<210> SEQ ID NO 14
<211> LENGTH: 8
<212> TYPE: PRT
<213> ORGANISM: Artificial Sequence
<220> FEATURE:
<223> OTHER INFORMATION: VH CDR1

<400> SEQUENCE: 14

Gly Tyr Thr Phe Thr Glu Tyr Thr
1               5
```

```
<210> SEQ ID NO 15
<211> LENGTH: 8
<212> TYPE: PRT
<213> ORGANISM: Artificial Sequence
<220> FEATURE:
<223> OTHER INFORMATION: VH CDR2

<400> SEQUENCE: 15

Ile Asn Pro Asn Asn Gly Gly Thr
1               5
```

```
<210> SEQ ID NO 16
<211> LENGTH: 10
<212> TYPE: PRT
<213> ORGANISM: Artificial Sequence
<220> FEATURE:
<223> OTHER INFORMATION: VH CDR3

<400> SEQUENCE: 16

Ala Arg Ser Tyr Tyr Gly Tyr Val Asp Tyr
1               5                   10

<210> SEQ ID NO 17
<211> LENGTH: 7
<212> TYPE: PRT
<213> ORGANISM: Artificial Sequence
<220> FEATURE:
<223> OTHER INFORMATION: VL CDR1

<400> SEQUENCE: 17

Ala Ser Ser Ser Ile Tyr Tyr
1               5

<210> SEQ ID NO 18
<211> LENGTH: 3
<212> TYPE: PRT
<213> ORGANISM: Artificial Sequence
<220> FEATURE:
<223> OTHER INFORMATION: VL CDR2

<400> SEQUENCE: 18

Asp Thr Ser
1

<210> SEQ ID NO 19
<211> LENGTH: 9
<212> TYPE: PRT
<213> ORGANISM: Artificial Sequence
<220> FEATURE:
<223> OTHER INFORMATION: VL CDR3

<400> SEQUENCE: 19

Gln Gln Trp Ser Ser Asn Pro Phe Thr
1               5
```

ISOLATED ANTIBODIES AGAINST INTERLEUKIN-17 RECEPTOR B (IL-17RB) FOR CANCER THERAPY

RELATED APPLICATIONS

The present application is a national stage filing under 35 U.S.C. § 371 of International Application No. PCT/US2015/038565, filed Jun. 30, 2015, which claims priority under 35 U.S.C. § 119(e) to U.S. Provisional Patent Application No. 62/019,421, filed Jun. 30, 2014, the disclosures of each of which are herein incorporated by reference in their entirety.

FIELD OF THE INVENTION

The present invention relates generally to cancer therapy. The invention is more specifically related to antagonists specific for interleukin-17B receptor (IL-17RB) and its ligand IL-17B. In particular, the invention relates to potent neutralizing antibodies specific for IL-17RB and IL-17B and their manufacture and use. In particular, the invention relates to antisense nucleic acids specific for inhibition of IL-17RB and IL-17B and their manufacture and use. The invention also relates to compositions for the prevention and treatment of cancer, in particular breast cancer and pancreatic cancer.

BACKGROUND OF THE INVENTION

Breast cancer is responsible for the second overall cause of cancer-related deaths among women. In 2005 an estimated 212,000 new cases of invasive and 58,000 new cases of non-invasive breast cancer were diagnosed, with 40,000 deaths.

Currently, prevention of breast cancer predominantly involves reducing modifiable risks including early detection through physical examination and mammograms, avoidance of unnecessary post-menopausal hormone therapy, reduction in alcohol consumption, loss of weight, increase in physical activity, and genetic testing for mutations of the breast cancer type 1 and type 2 susceptibility genes (BRCA1 and BRCA2, respectively). More aggressive approaches in high risk patients include chemoprevention with tamoxifen, raloxifene, and aromatase inhibitors as well as prophylactic bilateral mastectomy and oophorectomy.

Current therapeutic options for treatment of breast cancer, including metastatic breast cancer, include surgery (e.g. resection, autologous bone marrow transplantation), radiation therapy, chemotherapy (e.g. anthracyclines such as doxorubicin, alkylating agents such as cyclophosphamide and mitomycin C, taxanes such as paclitaxel and docetaxel, antimetabolites such as capecitabine, microtubule inhibitors such as the *vinca* alkaloid navelbine), endocrine therapy (e.g. antiestrogens such as tamoxifen, progestins such as medroxyprogesterone acetate and megastrol acetate, aromatase inhibitors such as aminoglutethamide and letrozole) and biologics (e.g. cytokines, immunotherapeutics such as monoclonal antibodies). Most commonly metastatic breast cancer is treated by one or a combination of chemotherapy (the most effective drugs including cyclophosphamide, doxorubicin, navelbine, capecitabine and mitomycin C) and endocrine therapy.

Pancreatic cancer is a malignant growth of the pancreas that mainly occurs in the cells of the pancreatic ducts. This disease is the ninth most common form of cancer, yet it is the fourth and fifth leading cause of cancer deaths in men and women, respectively. Cancer of the pancreas is almost always fatal, with a five-year survival rate that is less than 3%.

Current treatment procedures available for pancreatic cancer have not led to a cure, nor to a substantially improved survival time. Surgical resection has been the only modality that offers a chance at survival. However, due to a large tumor burden, only 10% to 25% of patients are candidates for "curative resection." For those patients undergoing a surgical treatment, the five-year survival rate is still poor, averaging only about 10%.

The interleukin 17 (IL-17) family comprises 6 interleukins (IL-17 A, IL-17B, IL-17C, IL-17D, IL-17E=IL-25 and IL-17F) and their receptors (IL-17RA, IL-17RB, IL-17RC, IL-17RD and IL-17RE) (Gaffen, S. L. (2009) "Structure and signalling in the IL-17 receptor family" Nature reviews. Immunology 9(8): 556-567).

WO 2013/186236 discloses increased expression of IL-17 isoforms and their receptors in cancer cells. Stimulation of cancer cells and increase in cancer cell migration and invasion by upregulation of IL-17B and IL-17RB were disclosed, but no antagonist specific for interleukin-17B receptor (IL-17RB) and its ligand IL-17B was reported.

There remains a need in the art for therapeutic agents that exhibit high selectivity for pancreatic cancer, breast cancer and a broad spectrum of cancers.

SUMMARY OF THE INVENTION

The present disclosure is based on the discovery of novel antagonists specific for interleukin-17B receptor (IL-17RB) and its ligand IL-17B.

Accordingly, one aspect of the present disclosure relates to a composition for treating cancers, the composition comprising an agent that is an antagonist of IL-17RB or IL-17B, in which the antagonist is an antibody or an antisense nucleic acid such as a small hairpin RNA (shRNA), a small interfering RNA (siRNA) or a micro RNA (miRNA).

In some embodiments, the antibody is a polyclonal antibody. In some embodiments, the antibody is a monoclonal antibody. In some embodiments, the antisense nucleic acid is a short hairpin RNA (shRNA). In certain embodiments, the shRNA comprises a sense strand selected from the nucleotide sequences of SEQ ID NOS: 5-9 and an antisense strand that hybridizes under stringent conditions to the sense strand. The shRNA described herein is capable of inhibiting expression of a gene selected from the group consisting of IL-17B and IL-17RB. In some embodiments, the composition further comprises a chemotherapeutic agent for treating tumors.

In another aspect, the present disclosure provides an shRNA for inhibiting cancer cell proliferation, which targets at an IL-17RB or IL-17B mRNA transcribed from the DNA sequence shown in SEQ ID NO:1 or 3, respectively.

In some embodiments, the shRNA comprises a nucleic acid sequence selected from the group consisting of SEQ ID NOS: 5-9.

The present disclosure also relates to a nucleic acid from which the shRNA described herein is transcribed, and a vector comprising the nucleic acid.

In another aspect, the present disclosure provides therapeutic methods for the treatment and prevention of cancer by administering to a subject in need of such treatment a therapeutically effective amount of a composition that includes an antibody or an antisense nucleic acid described herein. Also provided is use of a composition that includes an antibody or an antisense nucleic acid described herein for manufacturing a medicament for treating cancer.

In some embodiments, the antisense nucleic acid reduces the expression of IL-17RB or IL-17B. Examples of the antisense nucleic acid includes, but not limited to, a small hairpin RNA (shRNA), a small interfering RNA (siRNA) and a micro RNA (miRNA).

In some embodiments, the subject (e.g., a human patient) in need of the treatment is diagnosed with, suspected of having, or at risk for cancer. Examples of the cancer include, but are not limited to, pancreatic cancer, breast cancer, colorectal cancer, liver cancer, kidney cancer, head and neck cancer, esophageal cancer, gastric cancer, biliary tract cancer, gallbladder and bile duct cancer, lung cancer, mammary cancer, ovarian cancer, cervical cancer, uterine body cancer, bladder cancer, prostate cancer, testicular tumor, osteogenic and soft-tissue sarcomas, leukemia, malignant lymphoma, multiple myeloma, skin cancer, brain tumor and plura malignant mesothelioma. In preferred embodiments, the cancer is breast cancer or pancreatic cancer.

In another aspect, the present disclosure relates to an isolated monoclonal antibody against IL-17RB that binds to an epitope located between amino acids 18 and 289 in an extracellular domain of IL-17RB, or an antigenic epitope therein. This anti-IL-17RB antibody can be a full-length antibody or an antigen-binding fragment thereof, which includes, but is not limited to, a Fab fragment, a F(ab')2 fragment, or a single-chain Fv fragment. The monoclonal antibody described herein is capable of neutralizing an IL-17RB (i.e., binding to the IL-17RB and blocking the signal transduction mediated by the receptor) and can be a naturally-occurring antibody (e.g., a monoclonal antibody), an antigen-binding fragment thereof, or a genetically engineered antibody (e.g., human antibody, a humanized antibody, a chimeric antibody, a mouse antibody or a single-chain antibody) that neutralizes IL-17RB, i.e., binding to either antigen and blocking the signaling pathway mediated by it.

In some embodiments, the anti-IL-17RB antibody described herein comprises a heavy chain variable region ($V_H$) that comprises a $V_H$ complementarity determining region (CDR) 1 set forth as SEQ ID NO: 14, a $V_H$ CDR2 set forth as SEQ ID NO: 15, and a $V_H$ CDR3 set forth as SEQ ID NO: 16. Alternatively or in addition, the anti-IL-17RB antibody can comprise a light chain variable region ($V_L$) that comprises a $V_L$ CDR1 set forth as SEQ ID NO: 17, a $V_L$ CDR2 set forth as SEQ ID NO: 18, and a $V_L$ CDR3 set forth as SEQ ID NO: 19.

In other embodiments, the antibody comprises a $V_H$ that is at least 85% (e.g., 90%, 95%, 97%, 98%, or 99%) identical to SEQ ID NO:12. Alternatively or in addition, the anti-IL-17RB antibody comprises a $V_L$ that is at least 85% (e.g., 90%, 95%, 97%, 98%, or 99%) identical to SEQ ID NO:13. The anti-IL-17RB antibody binds to the same epitope as an anti-IL-17RB antibody having a $V_H$ set forth as SEQ ID NO:12 and a $V_L$ set forth as SEQ ID NO:13. In one example, the anti-IL-17RB antibody comprises a $V_H$ set forth as SEQ ID NO: 12 and a $V_L$ set forth as SEQ ID NO:13.

Nucleic acid molecules encoding such antibodies, and vectors and cells carrying such nucleic acids are also provided.

In one aspect, the present disclosure provides an isolated nucleic acid comprising a nucleotide sequence encoding an antibody heavy chain variable region ($V_H$) that comprises a $V_H$ complementarity determining region (CDR) 1 set forth as SEQ ID NO: 14, a $V_H$ CDR2 set forth as SEQ ID NO: 15, and a $V_H$ CDR3 set forth as SEQ ID NO: 16, and/or a nucleotide sequence encoding an antibody light chain variable region ($V_L$) that comprises a $V_L$ complementarity determining region (CDR1) set forth as SEQ ID NO: 17, a $V_L$ CDR2 set forth as SEQ ID NO: 18, and a $V_L$ CDR3 set forth as SEQ ID NO: 19.

Also provided here are vectors (e.g., expression vectors) comprising any of the nucleic acids described herein, and host cells comprising such vectors. In some examples, a vector (e.g., an expression vector) described herein comprises nucleotide sequences encoding both the heavy chain and light chain of any of the anti-IL-17RB antibodies described herein. In other examples, the nucleotide sequences encoding the heavy chain and light chain are located on different vectors.

In another aspect, the present disclosure provides methods for preparing any of the anti-IL-17RB antibodies described herein, the methods comprising culturing a host cell comprising expression vector(s) encoding the heavy and light chains of the antibody, and collecting the cultured cells for purification of the antibodies thus produced. Such a method can further comprise isolating the antibodies from either the cultured cells or the culture medium.

Further, the present disclosure provides compositions (e.g., pharmaceutical compositions) comprising any of the anti-IL-17RB antibodies described herein or any of the nucleic acids or vectors described herein, and a carrier, such as a pharmaceutically acceptable carrier.

In some embodiments, the anti-IL-17RB antibody disclosed herein is a mouse monoclonal antibody D9, an antigen-binding fragment thereof, or a functional equivalent thereof. In some embodiments, the anti-IL-17RB antibody disclosed herein is a chimeric monoclonal antibody cD9, an antigen-binding fragment thereof, or a functional equivalent thereof.

Also within the scope of this disclosure are (a) a pharmaceutical composition containing one or more agents that suppresses IL-17RB activity for use in treating an IL-17RB-mediated proliferation disorder, and (b) uses thereof in manufacturing a medicament for treating cancer.

In another aspect, the present disclosure provides methods for reducing symptoms of an IL-17RB-mediated proliferation disorder. The method of the invention comprises the steps of: (1) identifying a subject in need of such treatment and (2) administering to said subject a sufficient amount of an antibody described herein, wherein the amount of antibody is sufficient to reduce the expression of IL-17RB in a therapeutic manner.

In some embodiments, the identifying step is performed by an antibody against IL-17RB such as A81 or antibodies described herein.

In some embodiments, the IL-17RB-mediated proliferation disorder is cancer. Examples of cancers include, but not limited to, pancreatic cancer, breast cancer, colorectal cancer, liver cancer, kidney cancer, head and neck cancer, esophageal cancer, gastric cancer, biliary tract cancer, gallbladder and bile duct cancer, lung cancer, mammary cancer, ovarian cancer, cervical cancer, uterine body cancer, bladder cancer, prostate cancer, testicular tumor, osteogenic and soft-tissue sarcomas, leukemia, malignant lymphoma, multiple myeloma, skin cancer, brain tumor and plura malignant mesothelioma. In preferred embodiments, the cancer is breast cancer and pancreatic cancer.

The method of the invention may additionally comprise the use administration of a second therapeutic agent. In some embodiments, the second therapeutic agent is a nucleic acid is selected from a small hairpin RNA (shRNA), a small interfering RNA (siRNA), a micro RNA (miRNA), an antisense polynucleotide, and a ribozyme.

These and other aspects will become apparent from the following description of the preferred embodiment taken in conjunction with the following drawings, although variations and modifications therein may be affected without departing from the spirit and scope of the novel concepts of the disclosure.

BRIEF DESCRIPTION OF THE FIGURES

The following drawings form part of the present specification and are included to further demonstrate certain aspects of the present disclosure, the inventions of which can be better understood by reference to one or more of these drawings in combination with the detailed description of specific embodiments presented herein.

DETAILED DESCRIPTION OF THE INVENTION

Definitions

Figure 1:
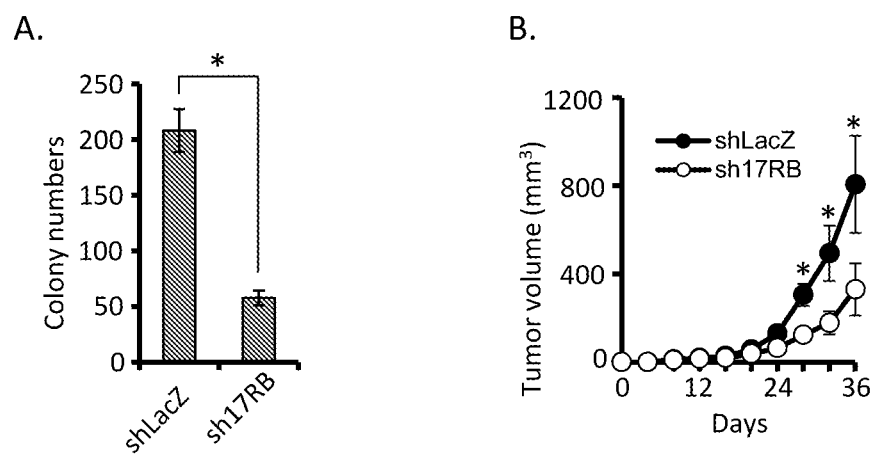
FIG. 1 shows high expression of IL-17RB promotes breast tumorigenesis. (A) Soft agar colony formation assay showed that depletion of IL-17RB by its corresponding short hairpin shRNA (sh17RB) impaired the ability of anchorage independent growth in MDA-MB-361 cells. (B) Xenograft tumorigenesis assay using NOD/SCID/$\gamma^{null}$ mice injected with MDA-MB-361 shLacZ control or shIL-17RB cells.
Figure 2:
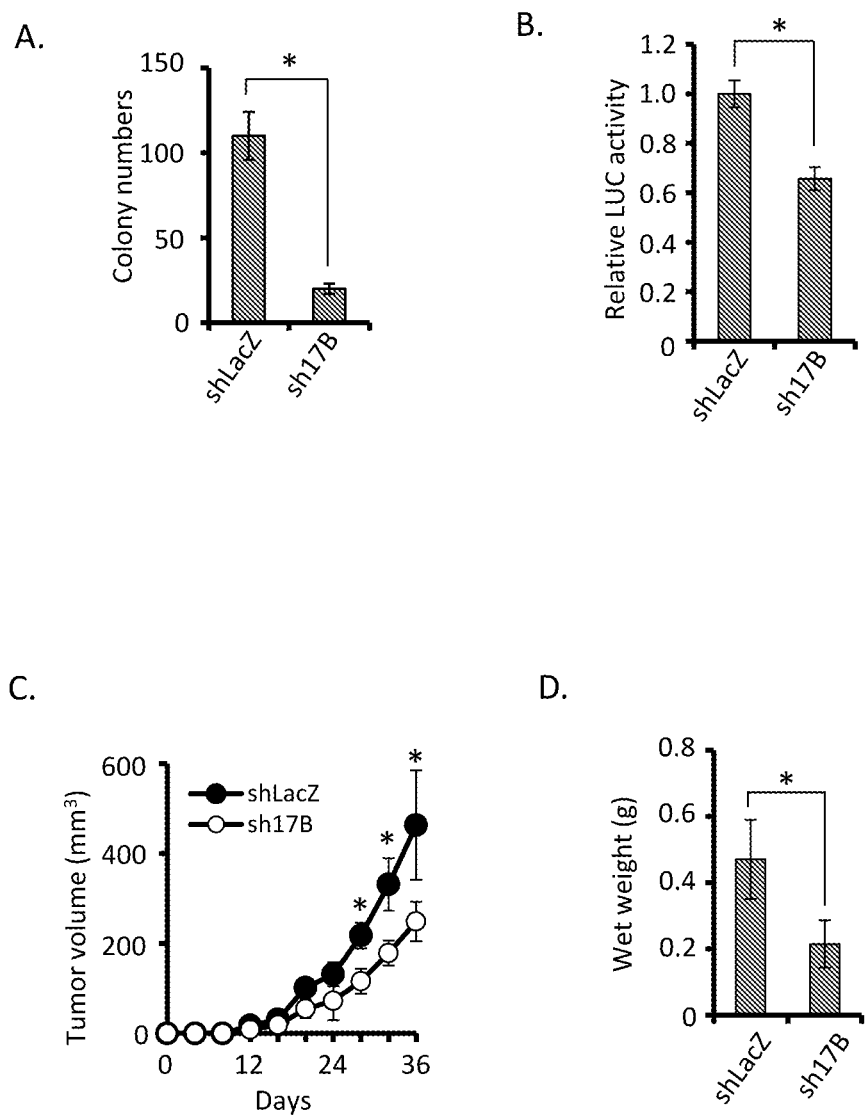
FIG. 2 shows IL-17B enhanced tumorigenic activity through IL-17RB. (A) Knockdown IL-17B by its corresponding short hairpin shRNA (sh17B) inhibited the colony formation ability of MDA-MB-361 cells. (B) The NF-κB promoter activity was decreased in IL-17B depleted MDA-MB-361 cells. (C) Tumorigenesis assay of NOD/SCID/$\gamma^{null}$ mice injected with MDA-MB-361 shLacZ control or sh17B cells. Depletion of IL-17B reduced tumor growth. (D) IL-17B depletion reduced the weight of MDA-MB-361 derived tumor.

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Antibodies: A Laboratory Manual, by Harlow and Lanes (Cold Spring Harbor Laboratory Press, 1988); and Handbook Of Experimental Immunology, Volumes I-IV (D. M. Weir and C. C. Blackwell, eds., 1986).

As used herein and in the appended claims, the singular forms "a," "and," and "the" include plural referents unless the context clearly dictates otherwise. Thus, for example, "a transport enhancer" encompasses a plurality of transport enhancers as well as a single transport enhancer. Reference to "a chelating agent" includes reference to two or more chelating agents as well as a single chelating agent, and so forth. In this specification and in the claims that follow, reference will be made to a number of terms, which shall be defined to have the following meanings:

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause. Unless otherwise indicated herein, either explicitly or by implication, if the term "treatment" (or "treating") is used without reference to possible prevention, it is intended that prevention be encompassed as well.

"Optional" or "optionally present"—as in an "optional substituent" or an "optionally present additive" means that the subsequently described component (e.g., substituent or additive) may or may not be present, so that the description includes instances where the component is present and instances where it is not.

By "pharmaceutically acceptable" is meant a material that is not biologically or otherwise undesirable, e.g., the material may be incorporated into a formulation of the invention without causing any undesirable biological effects or interacting in a deleterious manner with any of the other components of the dosage form formulation. However, when the term "pharmaceutically acceptable" is used to refer to a pharmaceutical excipient, it is implied that the excipient has met the required standards of toxicological and manufacturing testing and/or that it is included on the Inactive Ingredient Guide prepared by the U.S. Food and Drug Administration. As explained in further detail infra, "pharmacologically active" (or simply "active") as in a "pharmacologically active" derivative or analog refers to derivative or analog having the same type of pharmacological activity as the parent agent.

The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

The following definitions are useful in understanding the present invention:

As used herein, the term "antigen" is defined as any substance capable of eliciting an immune response.

As used herein, the term "immunogen" refers to an antigen or a substance capable of inducing production of an antigen, such as a DNA vaccine.

As used herein, the term "immunogenicity" refers to the ability of an immunogen, antigen, or vaccine to stimulate an immune response.

The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

A "neutralizing antibody" may inhibit or reduce the levels of IL-17RB or IL-17B in a cell. The inhibitory concentration of the monoclonal antibody may be less than about 25 mg/ml to neutralize about 50% of the target molecule levels in a cell.

As used herein, the term "immunotherapy" refers to an array of treatment strategies based upon the concept of modulating the immune system to achieve a prophylactic and/or therapeutic goal.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Ten and Tristram G. Parslow (eds.), Appleton & Lange, Norwalk, Conn., 1994, page 71, and Chapter 6.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. e al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_H$ when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

In some aspects, the alternative EBV immortalization method described in WO2004/076677 is used. Using this method, B-cells producing the antibody of the invention can be transformed with EBV in the presence of a polyclonal B cell activator. Transformation with EBV is a standard technique and can easily be adapted to include polyclonal B cell activators. Additional stimulants of cellular growth and differentiation may be added during the transformation step to further enhance the efficiency. These stimulants may be cytokines such as IL-2 and IL-15. In a particularly preferred aspect, IL-2 is added during the immortalization step to further improve the efficiency of immortalization, but its use is not essential.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). The present invention provides variable domain antigen-binding sequences derived from human antibodies. Accordingly, chimeric antibodies of primary interest herein include antibodies having one or more human antigen binding sequences (e.g., CDRs) and containing one or more sequences derived from a non-human antibody, e.g., an FR or C region sequence. In addition, chimeric antibodies of primary interest herein include those comprising a human variable domain antigen binding sequence of one antibody class or subclass and another sequence, e.g., FR or C region sequence, derived from another antibody class or subclass.

Chimeric antibodies of interest herein also include those containing variable domain antigen-binding sequences related to those described herein or derived from a different species, such as a non-human primate (e.g., Old World Monkey, Ape, etc). Chimeric antibodies also include primatized and humanized antibodies.

Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332: 323-329 (1988); and Presta, Curr. Op. Struct. Biol. 2:593-596 (1992).

A "humanized antibody" is generally considered to be a human antibody that has one or more amino acid residues introduced into it from a source that is non-human. These non-human amino acid residues are often referred to as "import" residues, which are typically taken from an "import" variable domain. Humanization is traditionally performed following the method of Winter and co-workers (Jones et al., Nature, 321:522-525 (1986); Reichmann et al., Nature, 332:323-327 (1988); Verhoeyen et al., Science, 239:1534-1536 (1988)), by substituting import hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species.

A "human antibody" is an antibody containing only sequences present in an antibody naturally produced by a human. However, as used herein, human antibodies may comprise residues or modifications not found in a naturally occurring human antibody, including those modifications and variant sequences described herein. These are typically made to further refine or enhance antibody performance.

An "intact" antibody is one that comprises an antigen-binding site as well as a $C_L$ and at least heavy chain constant domains, $C_H1$, $C_H2$ and $C_H3$. The constant domains may be native sequence constant domains (e.g., human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

The phrase "functional fragment or analog" of an antibody is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, $Fc_{gamma}RI$.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment that roughly corresponds to two disulfide linked Fab fragments having divalent antigen-binding activity and is still capable of cross-linking antigen. Fab' fragments differ from Fab fragments by having additional few residues at the carboxy terminus of the C$_H$1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the V$_H$ and V$_L$ antibody domains connected into a single polypeptide chain. Preferably, the sFv polypeptide further comprises a polypeptide linker between the V$_H$ and V$_L$ domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the V$_H$ and V$_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the V$_H$ and V$_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

Domain antibodies (dAbs), which can be produced in fully human form, are the smallest known antigen-binding fragments of antibodies, ranging from 11 kDa to 15 kDa. dAbs are the robust variable regions of the heavy and light chains of immunoglobulins (VH and VL respectively). They are highly expressed in microbial cell culture, show favourable biophysical properties including solubility and temperature stability, and are well suited to selection and affinity maturation by in vitro selection systems such as phage display. dAbs are bioactive as monomers and, owing to their small size and inherent stability, can be formatted into larger molecules to create drugs with prolonged serum half-lives or other pharmacological activities. Examples of this technology have been described in WO9425591 for antibodies derived from Camelidae heavy chain Ig, as well in US20030130496 describing the isolation of single domain fully human antibodies from phage libraries.

As used herein, an antibody that "internalizes" is one that is taken up by (i.e., enters) the cell upon binding to an antigen on a mammalian cell (e.g., a cell surface polypeptide or receptor). The internalizing antibody will of course include antibody fragments, human or chimeric antibody, and antibody conjugates. For certain therapeutic applications, internalization in vivo is contemplated. The number of antibody molecules internalized will be sufficient or adequate to kill a cell or inhibit its growth, especially an cancer cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the cancer cell.

As used herein, an antibody is said to be "immunospecific," "specific for" or to "specifically bind" an antigen if it reacts at a detectable level with the antigen, preferably with an affinity constant, Ka, of greater than or equal to about $10^4$ M$^{-1}$, or greater than or equal to about $10^5$ M$^{-1}$, greater than or equal to about $10^6$ M$^{-1}$, greater than or equal to about $10^7$ M$^{-1}$, or greater than or equal to $10^8$ M$^{-1}$. Affinity of an antibody for its cognate antigen is also commonly expressed as a dissociation constant K$_D$, and in certain embodiments, IL-17RB or IL-17B antibody specifically binds to a IL-17RB or IL-17B polypeptide if it binds with a K$_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M. Affinities of antibodies can be readily determined using conventional techniques, for example, those described by Scatchard et al. (*Ann. N.Y. Acad. Sci. USA* 51:660 (1949)).

Binding properties of an antibody to antigens, cells or tissues thereof may generally be determined and assessed using immunodetection methods including, for example, immunofluorescence-based assays, such as immuno-histo-chemistry (IHC) and/or fluorescence-activated cell sorting (FACS).

An antibody having a "biological characteristic" of a designated antibody is one that possesses one or more of the biological characteristics of that antibody which distinguish it from other antibodies. For example, in certain embodiments, an antibody with a biological characteristic of a designated antibody will bind the same epitope as that bound by the designated antibody and/or have a common effector function as the designated antibody.

The term "antagonist" antibody is used in the broadest sense, and includes an antibody that partially or fully blocks, inhibits, or neutralizes a biological activity of an epitope, polypeptide, or cell that it specifically binds. Methods for identifying antagonist antibodies may comprise contacting a polypeptide or cell specifically bound by a candidate antagonist antibody with the candidate antagonist antibody and measuring a detectable change in one or more biological activities normally associated with the polypeptide or cell.

An "antibody that inhibits the growth of cancer cells" or a "growth inhibitory" antibody is one that binds to and results in measurable growth inhibition of cancer cells expressing or capable of expressing a IL-17RB or IL-17B epitope bound by an antibody. Preferred growth inhibitory antibodies inhibit growth of cancer cells by greater than 20%, preferably from about 20% to about 50%, and even more preferably, by greater than 50% (e.g., from about 50% to about 100%) as compared to the appropriate control, the control typically being cancer cells not treated with the antibody being tested. Growth inhibition can be measured at an antibody concentration of about 0.1 to about 30 µg/ml or about 0.5 nM to 200 nM in cell culture, where the growth inhibition is determined 1-10 days after exposure of the cancer cells to the antibody. Growth inhibition of cancer cells in vivo can be determined in various ways known in the art. The antibody is growth inhibitory in vivo if administration of the antibody at about 1 µg/kg to about 100 mg/kg body weight results in reduction the percent of cancer cells or total number of cancer cells within about 5 days to 3 months from the first administration of the antibody, preferably within about 5 to 30 days.

An antibody that "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). Preferably the cell is an cancer cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody that induces apoptosis is one that results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, $Annu.$ $Rev.$ $Immunol$ 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., $Proc.$ $Natl.$ $Acad.$ $Sci.$ (USA) 95:652-656 (1998).

"Fc receptor" or "FcR" describes a receptor that binds to the Fc region of an antibody. In certain embodiments, the FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FCγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes that express one or more FcRs and perform effector functions. Preferably, the cells express at least FcγRIII and perform ADCC effector function. Examples of human leukocytes that mediate ADCC include PBMC, NK cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) that are bound to their cognate antigen. To assess complement activation, a CDC assay, e.g., as described in Gazzano-Santoro et al., J. Immunol. Methods 202:163 (1996), may be performed.

As used herein, the term "cytokine" refers to any of numerous small, secreted proteins that regulate the intensity and duration of the immune response by affecting immune cells differentiation process usually involving changes in gene expression by which a precursor cell becomes a distinct specialized cell type. Cytokines have been variously named as lymphokines, interleukins, and chemokines, based on their presumed function, cell of secretion, or target of action. For example, some common interleukins include, but are not limited to, IL-17, IL-12, IL-18, IL-2, IFN-γ, TNF, IL-4, IL-10, IL-13, IL-21 and TGF-β.

As used herein, the term "epitope" is defined as the parts of an antigen molecule which contact the antigen binding site of an antibody or a T cell receptor.

As used herein, the term "vaccine" refers to a preparation that contains an antigen, consisting of whole disease-causing organisms (killed or weakened) or components of such organisms, such as proteins, peptides, or polysaccharides, that is used to confer immunity against the disease that the organisms cause. Vaccine preparations can be natural, synthetic or derived by recombinant DNA technology.

As used herein, the term "immunologic adjuvant" refers to a substance used in conjunction with an immunogen which enhances or modifies the immune response to the immunogen. α-GalCer analogs are used as immunologic adjuvants to modify or augment the effects of a vaccine by stimulating the immune system of a patient who is administered the vaccine to respond to the vaccine more vigorously. In an exemplary implementation, the analog C34 is used as an adjuvant. As used herein, the term "alum adjuvant" refers to an aluminum salt with immune adjuvant activity. This agent adsorbs and precipitates protein antigens in solution; the resulting precipitate improves vaccine immunogenicity by facilitating the slow release of antigen from the vaccine depot formed at the site of inoculation.

As used herein, the term "anti-tumor immunotherapy active agent" refers to antibody generated by a vaccine of the present disclosure that inhibits, reduces and/or eliminates tumors.

As used herein, the term "antigen specific" refers to a property of a cell population such that supply of a particular antigen, or a fragment of the antigen, results in specific cell proliferation.

The term "RNA interference" or "RNAi" refers to the silencing or decreasing of gene expression by RNAi agents (e.g., "short interfering RNA", "siRNA", "shRNA", "short interfering nucleic acid molecule", "short interfering oligonucleotide molecule", or "chemically-modified short interfering nucleic acid molecule"). The term "short interfering nucleic acid", "siNA", "short interfering RNA", "siRNA", "short interfering nucleic acid molecule", "short interfering oligonucleotide molecule", or "chemically-modified short interfering nucleic acid molecule" as used herein refers to any nucleic acid molecule capable of inhibiting or down regulating gene expression or viral replication, for example by mediating RNA interference (see, e.g., (Grimm, Adv. Drug Deliv. Rev., 61, 672, 2009; Gondi, J. Cell Physiol, 220, 285, 2009; Carthew, 136, 642, 2009; Jinek, 457, 405, 2009; Ghildiyal, Nat. Rev. Genet., 10, 94, 2009). RNAi is the process of sequence-specific, post-transcriptional gene silencing in cells, animals and plants, initiated by an RNAi agent that is homologous in its duplex region to the sequence of the to-be-silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be completely or partially inhibited.

In some embodiments, the RNAi agent can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The RNAi agent can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure, for example wherein the double stranded region is about 19 base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the RNAi agent is assembled from a single oligonucleotide, where the self-complementary sense and antisense regions of the RNAi agent are linked by means of a nucleic-acid-based or non-nucleic acid-based linker(s). The RNAi agent can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The RNAi agent can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active small nucleic acid molecule capable of mediating RNAi. The RNAi agent can also comprise a single stranded polynucleotide having nucleotide sequence complementary to nucleotide sequence in a target nucleic acid molecule or a portion thereof. For present purposes, RNAi agent molecules need not be limited to those molecules containing only naturally occurring RNA, but further encompasses chemically-modified nucleotides and non-nucleotides.

The term "RNAi agent" is meant to be equivalent to other terms used to describe nucleic acid molecules that are capable of mediating sequence specific RNAi, for example, short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term "RNAi" is meant to be equivalent to other terms used to describe sequence specific RNA interference, such as post transcriptional gene silencing, translational inhibition, or epigenetics. As used herein, "siRNA" frequently refers to artificial nucleotide sequences that are used in RNA interference therapy. Typically, an siRNA is a double-stranded nucleic acid molecule comprising two nucleotide strands, each strand having about 19 to about 28 nucleotides.

A short hairpin RNA (shRNA) is a sequence of RNA that makes a tight hairpin turn that can be used to silence gene expression via RNA interference. It is typical to use a vector to introduce shRNA into cells and to use a promoter (e.g., the U6 promoter) to ensure that the shRNA is expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs which match the siRNA that is bound to it.

MicroRNAs (miRNAs) are a class of endogenous, single or double-stranded, about 22 nucleotide-long RNA molecules that regulate as much as 30% of mammalian genes, with important roles in regulation of cellular differentiation, proliferation, and apoptosis. Specific patterns of up- and down-regulation of miRNAs in various human tumor types are recognized. miRNA represses protein production by blocking translation or causing transcript degradation.

The terms "gene knockdown", "knockdown", or "knockdown" are used interchangeably and refer to techniques by which the expression of one or more of an organism's genes is reduced, either through genetic modification (a change in the DNA of one of the organism's chromosomes) or by treatment with a reagent such as a short DNA or RNA oligonucleotide with a sequence complementary to either an mRNA transcript or a gene. Knockdown using RNAi agents changes gene expression through, inter alia, degradation of the mRNA, blocking of the mRNA translation, or blocking maturation of pre-mRNA to mRNA.

The terms "siRNA against (name of a gene)", "anti-(name of a gene) siRNA" are used interchangeably and refer to an siRNA that is directed at a gene for the purpose of silencing the gene.

The terms "expression" and "transfection" of the RNAi agents are used interchangeably, and refer to the activity of the RNAi agents after delivery inside the cell. A high expression or transfection indicates effective knockdown of the target protein or proteins. For siGLO, a green-fluorescent dsRNA molecule designed to be transported to the nucleus after delivery to the cytosol of a cell and after release from the vectors or endosomes as a free molecule, expression or transfection is indicated by the accumulation of green fluorescence in the nucleus of the cell.

The term "intracellular bioavailability of an RNAi agent" refers to the RNAi agent that is released intact, i.e., not degraded, from its carrier, endosomes or lysosomes, that is generally available for reaching the intracellular RNAi machinery, or that is functional in achieving its RNA interference action.

The term "RIDES" refers to a multi-component RNAi vector system that can be used for administration of RNAi agents. RIDES stands for RNAi delivery and expression system. One component of RIDES is a pegylated liposomal cationic RNAi vector, PCat liposomes. The other component of RIDES comprises one or more of paclitaxel, doxorubicin, other tubulin-active agents, or other topoisomerase inhibitors. The inclusion of one or more of these agents is to improve the delivery of RNAi vectors, including PCat-siRNA, to cells and to improve the release of RNAi from its carriers, endosomes, and lysosomes to the cytosol and the resulting gene silencing.

The term "vector" refers to a vehicle or other mechanism by which gene delivery or nucleic acid delivery can be accomplished. In certain embodiments, gene delivery or nucleic acid delivery, including RNAi agent delivery, can be achieved by a number of mechanisms including, for example, vectors derived from viral and non-viral sources, cation complexes, nanoparticles, liposomes, and the like.

The terms "carrier" and "vector" are used interchangeably, and refer to a vehicle. For example, an RNAi carrier refers to a vehicle for transport of RNAi, such as, for example, a liposome; an RNAi carrier liposome or an RNAi liposome carrier refers to a situation where a liposome is the carrier or vehicle of the RNAi; a pharmaceutically acceptable carrier is an art recognized term referring to a vehicle or medium for containing an agent, presumably a product with a therapeutic purpose.

The terms "drug" and "agent" are used interchangeably and refer to substance that is used for diagnosing, detecting, or monitoring tumors or proliferative disorders. The term "agent" includes small molecules, macromolecules (e.g., peptides, proteins, antibodies, or antibody fragments), nucleic acids (e.g., gene therapy constructs), recombinant viruses, nucleic acid fragments (including, e.g., synthetic nucleic acid fragments, siRNA molecules, antisense molecules), nanoparticles, and microparticles.

The terms "sub-therapeutic", "sub-cytotoxic" and "non-cytotoxic" are used interchangeably, and refer to doses or concentrations that are lower than those typically used for treatment in humans or cause cytotoxicity to cultured cells used in the experiments. For example, a sub-therapeutic dose in a human subject for paclitaxel is less than about 120 mg/m$^2$, for docetaxel is less than about 72 mg/m$^2$, for vincristine is less than about 1 mg/m$^2$, for colchicine is less than about 3 mg oral dose, and for doxorubicin is less than about 60 mg/m$^2$.

The term "apoptosis" refers to any non-necrotic, well-regulated form of cell death, as defined by criteria well established in the art.

Within certain embodiments of this disclosure, pharmaceutical compositions and methods are provided that feature the presence or administration of one or more RNAi molecules or other dsRNA or analogs thereof of this disclosure, possibly combined, complexed, or conjugated with a polypeptide, optionally formulated with a pharmaceutically-acceptable carrier, such as a diluent, stabilizer, buffer, or the like. The negatively charged dsRNA molecules of this disclosure may be administered to a patient by any standard means, with or without stabilizers, buffers, or the like, to form a composition suitable for treatment. When it is desired to use a liposome delivery mechanism, standard protocols for formation of liposomes can be followed. The compositions of the present disclosure may also be formulated and used as a tablet, capsule or elixir for oral administration, suppository for rectal administration, sterile solution, or suspension for injectable administration, either with or without other compounds known in the art. Thus, dsRNAs of the present disclosure may be administered in any form, such as nasally, transdermally, parenterally, or by local injection.

The terms "cancer", "tumor cell", "tumor", "leukemia", or "leukemic cell" are used interchangeably and refer to any neoplasm ("new growth"), such as, for example, a carcinoma (derived from epithelial cells), adenocarcinoma (derived from glandular tissue), sarcoma (derived from connective tissue), lymphoma (derived from lymph tissue), or cancer of the blood (e.g., leukemia or erythroleukemia). The terms "cancer" or "tumor cell" also are intended to encompass cancerous tissue or a tumor mass, which shall be construed as a compilation of cancer cells or tumor cells, and are intended to encompass cancers or cells that may be either benign, premalignant, or malignant. Typically a cancer or tumor cell exhibits various art recognized hallmarks such as, for example, growth factor independence, lack of cell/cell contact growth inhibition, and/or abnormal karyotype. By contrast, a normal cell typically can only be passaged in culture for a finite number of passages and/or exhibits various art-recognized hallmarks attributed to normal cells (e.g., growth factor dependence, contact inhibition, and/or a normal karyotype). Genetically normal cells that are physically part of the aberrant growth and frequently play an integral role in the proliferative process are also referred to as cancer cells or tumor cells. This includes, inter alia, stromal and endothelial cells that proliferate under influence of tumor-secreted factors, and stromal cells that stimulate proliferation of epithelial tumor cells.

The term "cell" includes any eukaryotic cell, such as, for example, somatic or germ line mammalian cells, or cell lines, e.g., HeLa cells (human), NIH3T3 cells (murine), embryonic stem cells, and cell types such as hematopoietic stem cells, myoblasts, hepatocytes, lymphocytes, and epithelial cells and, e.g., the cell lines described herein.

The term "subject" is intended to include human and non-human animals (e.g., inter alia, mice, rats, rabbits, cats, dogs, livestock, and primates).

The term "particles" refers to nanoparticles, microparticles, or both nanoparticles and microparticles.

The term "microparticles" refers to particles of about 0.1 μm to about 100 μm, about 0.5 μm to about 50 μm, 0.5 μm to about 20 μm in size, advantageously, particles of about 1 μm to about 10 μm in size, about 5 μm in size, or mixtures thereof. The microparticles may comprise macromolecules such as RNAi agents, for example. Typically microparticles can be administered locally or regionally, for example.

The term "nanoparticles" refers to particles of about 0.1 nm to about 1 µm, 1 nm to about 1 µm, about 10 nm to about 1 µm, about 50 nm to about 1 µm, about 100 nm to about 1 µm. The nanoparticles may comprise macromolecules such as RNAi agents, for example. Typically, nanoparticles can be administered to a patient via local, regional, or systemic administration.

Disclosed herein are the compositions and methods for treating cancers associated with signaling pathways mediated by the IL-17RB or IL-17B. An agent that suppresses IL-17RB or IL-17B activity includes but is not limited to: (i) an antibody that neutralizes IL-17RB or IL-17B activity or cellular concentrations via, e.g., binding to IL-17RB or IL-17B, or (ii) an antisense nucleic acid or RNAi of the IL-17RB or IL-17B.

Sequences

Table 1 below shows the amino acid sequence of IL17RB (interleukin 17 receptor B) and the nucleic acid sequence of the gene encoding it. The extracellular domain (amino acid 18-289) used for the generation of polyclonal and monoclonal antibodies are underlined.

TABLE 1

IL-17RB; interleukin-17 receptor B [Homo sapiens (human)] NCBI-GeneID: 55540
Source: www.genome.jp/dbget-bin/www_bget?hsa:55540

Amino Acid Sequence (502 aa)
MSLVLLSLAALCRSAVPREPTVQCGSETGPSPEWMLQHDLIPGDLRDLRV
EPVTTSVATGDYSILMNVSWVLRADASIRLLKATKICVTGKSNFQSYSCV
RCNYTEAFQTQTRPSGGKWTFSYIGFPVELNTVYFIGAHNIPNANMNEDG
PSMSVNFTSPGCLDHIMKYKKKCVKAGSLWDPNITACKKNEETVEVNFTT
TPLGNRYMALIQHSTIIGFSQVFEPHQKKQTRASVVIPVTGDSEGATVQL
TPYFPTCGSDCIRHKGTVVLCPQTGVPFPLDNNKSKPGGWLPLLLLSLLV
ATWVLVAGIYLMWRHERIKKTSFSTTTLLPPIKVLVVYPSEICFHHTICY
FTEFLQNHCRSEVILEKWQKKKIAEMGPVQWLATQKKAADKVVFLLSNDV
NSVCDGTCGKSEGSPSENSQDLFPLAFNLFCSDLRSQIHLHKYVVVYFRE
IDTKDDYNALSVCPKYHLMKDATAFCAELLHVKQQVSAGKRSQACHDGCC
SL (SEQ ID NO: 1)

Nucleotide Sequence (1509 nucleotides)
atgtcgctcgtgctgctaagcctggccgcgctgtgcaggagcgccgtacc
ccgagagccgaccgttcaatgtggctctgaaactgggccatctccagagt
ggatgctacaacatgatctaatccccggagacttgagggacctccgagta
gaacctgttacaactagtgttgcaacaggggactattcaattttgatgaa
tgtaagctgggtactccggcagatgccagcatccgcttgttgaaggcca
ccaagatttgtgtgacgggcaaaagcaacttccagtcctacagctgtgtg
aggtgcaattacacagaggcctccagactcagaccagaccctctggtgg
taaatggacattttcctacatcggcttccctgtagagctgaacacagtct
atttcattgggccataatattcctaatgcaaatatgaatgaagatggc
ccttccatgtctgtgaatttcacctcaccaggctgcctagaccacataat
gaaatataaaaaaagtgtgtcaaggccggaagcctgtgggatccgaaca
tcactgcttgtaagaagaatgaggagacagtagaagtgaacttcacaacc
actccctgggaaacagatacatggctcttatccaacacagcactatcat
cgggttttccaggtgtttgagccacaccagaagaaacaaacgcgagcttc
agtggtgattccagtgactggggatagtgaaggtgctacaggtgcagctga
ctccatattttcctacttgtggcagcgactgcatccgacataaaggaaca
gttgtgctctgcccacaaacaggcgtccctttccctctggataacaacaa
aagcaagccgggaggctggctgcctctcctgctgtctctgctggtgg
ccacatgggtgctggtggcagggatctatctaatgtggaggcacgaaagg
atcaagaagacttccttttctaccaccacactactgccccccattaaggt
tcttgtggtttacccatctgaaatatgtttccatcacacaatttgttact
tcactgaatttcttcaaaaccattgcagaagtgaggtcatccttgaaaag
tggcagaaaaagaaaatagcagagatgggtccagtgcagtggcttgccac
tcaaaagaaggcagcagacaaagtcgtcttccttctttccaatgacgtca
acagtgtgtgcgatggtacctgtggcaagagcgagggcagtcccagtgag
aactctcaagacctcttccccctttgcctttaacctttttctgcagtgatct
aagaagccagattcatctgcacaaatacgtggtggtctactttagagaga
ttgatacaaaagacgattacaatgctctcagtgtctgccccaagtaccac TABLE 1-continued IL-17RB; interleukin-17 receptor B [Homo sapiens (human)] NCBI-GeneID: 55540
Source: www.genome.jp/dbget-bin/www_bget?hsa:55540 ctcatgaaggatgccactgctttctgtgcagaacttctccatgtcaagca
gcaggtgtcagcaggaaaaagatcacaagcctgccacgatggctgctgct
ccttgtag (SEQ ID NO: 2)

Table 2 below shows the amino acid sequence of IL-17B and the nucleic acid sequence of the gene encoding it.

TABLE 2

IL-17B; interleukin 17B [Homo sapiens (human)]
Gene ID: 27190
Source: www.genome.jp/dbget-bin/www_bget?hsa: 27190

Amino Acid seq (180 aa)
MDWPHNLLFLLTISIFLGLGQPRSPKSKRKGQGRPGPLAPGPHQVPLDLV
SRMKPYARMEEYERNIEEMVAQLRNSSELAQRKCEVNLQLWMSNKRSLSP
WGYSINHDPSRIPVDLPEARCLCLGCVNPFTMQEDRSMVSVPVFSQVPVR
RRLCPPPPRTGPCRQRAVMETIAVGCTCIF (SEQ ID NO: 3)

Nucleotide seq (543 nt)
atggactggcctcacaacctgctgtttcttcttaccatttccatcttcct
ggggctgggccagcccaggagcccaaaagcaagaggaagggcaagggc
ggcctgggcccctggccctggccctcaccaggtgccactggacctggtg
tcacggatgaaaccgtatgcccgcatggaggagtatgagaggaacatcga
ggagatggtggcccagctgaggaacagctcagagctggcccagagaaagt
gtgaggtcaactttgcagctgtggatgtccaacaagaggagcctgtctccc
tggggctacagcatcaaccacgaccccagccgtatcccgtggacctgcc
ggaggcacggtgcctgtgtctgggctgtgtgaacccttcaccatgcagg
aggaccgcagcatggtgagcgtgccggtgttcagccaggttcctgtgcgc
cgccgcctctgcccgccaccgccccgcacagggccttgccgccagcgcgc
agtcatggagaccatcgctgtgggctgcacctgcatcttctga
(SEQ ID NO: 4)

Anti-IL-17RB Antibodies

Described herein are isolated anti-IL-17RB antibodies targeting specific segments located in the extracellular domain of IL-17RB. The term "isolated antibody" used herein refers to an antibody substantially free from naturally associated molecules, i.e., the naturally associated molecules constituting at most 20% by dry weight of a preparation containing the antibody. Purity can be measured by any appropriate method, e.g., column chromatography, polyacrylamide gel electrophoresis, and HPLC. An antibody (interchangeably used in plural form) is an immunoglobulin molecule capable of specific binding to a target such as, for example, a carbohydrate, polynucleotide, lipid or polypeptide through at least one antigen recognition site located in the variable region of the immunoglobulin molecule. As used herein, the term "antibody" encompasses not only intact (e.g., full-length) polyclonal or monoclonal antibodies, but also antigen-binding fragments thereof (such as Fab, Fab', F(ab')₂ and Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins may be assigned to different classes.

There are five major classes of immunoglobulins: IgA, IgD, IgE, IgG and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma and mu, respectively. The subunit structures and three-dimensional configurations of different classes of immunoglobulins are well known.

The anti-IL-17RB antibodies described herein, which are useful in alleviating IL-17RB-mediated diseases, may be murine, rat, human or any other origin (including chimeric or humanized antibodies). In some examples, the antibodies comprise a modified constant region, such as a constant region that is immunologically inert, e.g., does not trigger complement mediated lysis or does not stimulate antibody-dependent cell mediated cytotoxicity (ADCC). In other embodiments, the constant region is modified as described in Eur. J. Immunol. (1999) 29:2613-2624; PCT Application No. PCT/GB99/01441; and/or UK Patent Application No. 9809951.8.

Any of the antibodies described herein may be either monoclonal or polyclonal. A "monoclonal antibody" refers to a homogenous antibody population, and a "polyclonal antibody" refers to a heterogeneous antibody population. These two terms do not limit the source of an antibody or the manner in which it is made.

In some embodiments, the antibodies described herein are chimeric antibodies, which can include a heavy constant region and a light constant region from human antibodies.

Chimeric antibodies may refer to antibodies having a variable region or part of variable region from a first species and a constant region from a second species. In some embodiments, in these chimeric antibodies, the variable region of both light and heavy chains may mimic the variable region of antibodies derived from one species of mammal (e.g., a non-human mammal such as mouse, rabbit and rat), while the constant portions may be homologous to the sequences in antibodies derived from another mammal such as a human. In some embodiments, amino acid modifications may be made in the variable region and/or the constant region.

In some embodiments, the antibodies provided herein are humanized antibodies. Humanized antibodies may refer to forms of non-human (e.g., murine) antibodies that are specific chimeric immunoglobulins, immunoglobulin chains or antigen-binding fragments 5 thereof that contain minimal sequence derived from non-human immunoglobulin.

Humanized antibodies may be human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some embodiments, Fv framework of region (FR) residues of the human immunoglobulin are replaced by corresponding non-human residues. Furthermore, the humanized antibodies may comprise residues that are found neither in the recipient antibodies nor in the imported CDR or framework sequences, but are included to further refine and optimize antibody performance. In some embodiments, humanized antibodies may comprise substantially all of at least one or two, variable domains, 5 in which all or substantially all of the CDR regions correspond to those of non-human immunoglobulins and all or substantially all of the FR regions are those of a human immunoglobulin consensus sequence. The humanized antibodies may also comprise at least a portion of an immunoglobulin constant region or domain (Fc), typically that of a human immunoglobulin. Antibodies may have Fc regions modified as described in WO 99/58572. o Other forms of humanized antibodies may have at least one CDR (one, two, three, four, five, six), which may be altered with respect to the original antibodies, which is also termed at least one CDR "derived from" at least one CDR from the original antibody. Humanized antibodies may also involve affinity maturation.

The antibodies disclosed herein are capable of binding to a newly identified antigenic segment of IL-17RB, i.e., the segment comprising the amino acids 18 and 289 in SEQ ID NO: 1, or an antigenic epitope therein. Such antibodies may be capable of binding to the just-noted antigenic segment/epitope located in the extracellular domain of IL-17RB.

In some embodiments, the anti-IL-17RB antibodies described herein specifically and/or preferentially bind to the antigenic 17RB segment or epitopes therein. An antibody that o "specifically binds" (used interchangeably herein) to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. In some of embodiments, an antibody that specifically binds to a first target antigen may or may not specifically or preferentially bind to a second target antigen. As such, "specific binding" or "preferential binding" does not necessarily require (although it can include) exclusive binding. In some embodiments, reference to binding means preferential binding.

The binding affinity of an anti-IL-17RB antibody, or an antigenic epitope therein may be less than any of about 100 nM, about 50 nM, about 10 nM, about 1 nM, about 500 pM, about 100 pM, or about 50 pM to any of about 2 pM. Binding affinity may be expressed $K_D$ or dissociation constant, and an increased binding affinity corresponds to a decreased $K_D$. One way of determining binding affinity of antibodies to IL-17RB is by measuring binding affinity of monofunctional Fab fragments of the antibody. To obtain monofunctional Fab fragments, an antibody (for example, IgG) may be cleaved with papain or expressed recombinantly. The affinity of an anti-IgE Fab fragment of an antibody may be determined by surface plasmon resonance (BIAcore3000 surface plasmon resonance (SPR) system, BIAcore, INC, Piscaway N.J.). Kinetic association rates ($k_{on}$) and dissociation rates ($k_{off}$) (generally measured at 25° C.) may be obtained; and equilibrium dissociation constant ($K_D$) values may be calculated as $k_{off}/k_{on}$.

An antibody that neutralizes the activity of IL-17RB can bind to the receptor and suppress signal transduction mediated by the receptor (e.g., reducing the IL-17RB receptor-mediated signaling by at least 20%, 30%, 40%, 50%, 60%, 70%, 80%, 90% or greater) The term "antibody" used herein includes intact immunoglobulin molecules, e.g., IgG, IgA, and IgM, antigen binding fragments thereof, e.g., Fab, F(ab')2, and Fv, and genetically engineered antibody molecules, e.g., chimeric antibody, humanized antibody, scFv (single chain antibody), dAb (domain antibody; see Ward, et. al. (1989) Nature, 341: 544), and bi-specific antibody.

The antibody used in the treatments described herein can be either monoclonal or polyclonal. A "monoclonal antibody" refers to a homogenous antibody population and a "polyclonal antibody" refers to a heterogenous antibody population. These two terms do not limit the source of an antibody or the manner in which it is made.

In one example, the IL-17RB-neutralizing antibody is a humanized antibody. A humanized antibody contains a human immunoglobulin (i.e., recipient antibody) in which regions/residues responsible for antigen binding (e.g., the complementarity determining regions, particularly the specificity-determining residues therein) are replaced with those from a non-human immunoglobulin (i.e., donor antibody). Methods to identify regions/residues in the heavy and light chains of an antibody are well known in the art. See, e.g., Almagro, J. Mol. Recognit. 17:132-143 (2004); and Chothia et al., J. Mol. Biol. 227:799-817 (1987). In some instances, one or more residues inside a framework region of the recipient antibody are also replaced with those from the donor antibody. A humanized antibody may also contain residues from neither the recipient antibody nor the donor antibody. These residues are included to further refine and optimize antibody performance.

In some embodiments, the IL-17RB-neutralizing antibody is mouse monoclonal antibody mAbD9, an antigen-binding fragment thereof, or a functional equivalent of mAbD9.

In some embodiments, the IL-17RB-neutralizing antibody is chimeric monoclonal antibody mAb cD9, an antigen-binding fragment thereof, or a functional equivalent of mAb cD9.

The mAb D9 is a mouse monoclonal antibody, produced by the hybridoma cell line. The mAb cD9 is a chimeric monoclonal antibody, produced by the hybridoma cell line. Antibodies binding to the same epitope as D9 and cD9 are also within the scope of this disclosure.

TABLE 3

Amino acid and nucleotide sequences of antibodies D9 and cD9 heavy chain variable region ($V_H$), light chain variable region ($V_L$), $V_H$ complementarity determining regions (CDRs), and $V_L$ complementarily determining regions (CDRs).

| SEQ ID NO | DESCRIPTION | SEQUENCE |
|---|---|---|
| 10 | $V_H$ nucleotide sequence | GAGGTTCAGC TGCAGCAGTC TGGACCTGAG CTGGTGAAGC CTGGGGCTTC AGTGAAGATA TCCTGCAAGA CTTCTGGATA CACCTTCACT GAATACACCA TCCACTGGGT GAAGCAGAAC CATGGAAAGA GCCTTGACTG GATTGGAGGT ATTAATCCTA ACAATGGTGG TACTACTTAC AACCAGGAGT TCAAGGGCAA GGCCACATTG ACTGTAGATA AGTCCTCCAG TACAGCCTAC ATGGAATTCC GCAGCCTGAC ATCTGAGGAT TCTGCAGTCT ATTACTGTGC AAGAAGTTAC TACGGCTACG TAGACTACTG GGGCCAAGGC ACCACTCTCA CCGCGGCC |
| 11 | $V_L$ nucleotide sequence | CAAATTGTTC TCACCCAGTC TCCAGCAATC ATGTCTGCAT CTCCAGGGGA GAAGGTCACC ATGACCTGCA GTGCCAGCTC AAGTATATAT TACATACACT GGTACCAGCA GAAGTCAGGC ACCTCCCCCA AAAGATGGAT TTATGACACA TCCAAGCTGG CTTCTGGAGT CCCTGCTCGC TTCAGTGGCA GTGGGTCTGG GACCTCTTAC TCTCTCACAA TCAGCAGCAT GGAGGCTGAA GATGCTGCCA CTTATTACTG CCAGCAGTGG AGTAGTAACC CATTCACGTT CGGCTCGGGG ACAAAATTGG AAATAAAA |
| 12 | $V_H$ amino acid sequence | EVQLQQSGPELVKPGASVKISCKTSGYTFTEYTIHWVKQNHGKSLDWIGGINPNNGGT TYNQEFKGKATLTVDKSSSTAYMEFRSLTSEDSAVYYCARSYYGYVDYWGQGTTLTAA |
| 13 | $V_L$ amino acid sequence | QIVLTQSPAIMSASPGEKVTMTCSASSSIYYIHWYQQKSGTSPKRWIYDTSKLASGVPAR FSGSGSGTSYSLTISSMEAEDAATYYCQQWSSNPFTFGSGTKLEIK |
| 14 | $V_H$ CDR1 | GYTFTEYT |
| 15 | $V_H$ CDR2 | INPNNGGT |
| 16 | $V_H$ CDR3 | ARSYYGYVDY |
| 17 | $V_L$ CDR1 | ASSSIYY |
| 18 | $V_L$ CDR2 | DTS |
| 19 | $V_L$ CDR3 | QQWSSNPFT |

A functional equivalent of mAb D9 or cD9 has the same epitope-binding specificity as mAb D9 or cD9 and exhibits at least 20% (e.g., 30%, 40%, 50%, 60%, 70%, 80%, 90%, or greater) of the activity of neutralizing IL-17RB as relative to mAb D9 or cD9. In some embodiments, a functional equivalent of mAb D9 or cD9 contains the same regions/residues responsible for antigen-binding as mAb D9 or cD9, such as the same specificity-determining residues in the CDRs or the whole CDRs.

The regions/residues that are responsible for antigen-binding can be identified from amino acid sequences of the heavy chain/light chain sequences of mAbD9 by methods known in the art. See, e.g., www.bioinf.org.uk/abs; Almagro, J. Mol. Recognit. 17:132-143 (2004); and Chothia et al., J. Mol. Biol. 227:799-817 (1987). A functional equivalent of mAbD9 can be a genetically engineered antibody derived from one of the monoclonal antibodies (e.g., chimeric, single-chain, or humanized).

Methods of making monoclonal and polyclonal antibodies and fragments thereof in animals are well known in the art. See, for example, Harlow and Lane, (1988) Antibodies: A Laboratory Manual, Cold Spring Harbor Laboratory, New York.

In general, to produce antibodies against a protein (e.g., IL-17RB), the protein or a fragment thereof, optionally coupled to a carrier protein, such as KLH, can be mixed with an adjuvant, and injected into a host animal. Antibodies produced in the animal can then be purified by peptide affinity chromatography. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, CpG, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*.

Polyclonal antibodies are present in the sera of the immunized subjects. Monoclonal antibodies can be prepared using standard hybridoma technology (see, for example, Kohler et al. (1975) Nature 256, 495; Kohler et al. (1976) Eur. J. Immunol. 6, 511; Kohler et al. (1976) Eur J Immunol 6, 292; and Hammerling et al. (1981) Monoclonal Antibodies and T Cell Hybridomas, Elsevier, N.Y.). In particular, monoclonal antibodies can be obtained by any technique that provides for the production of antibody molecules by continuous cell lines in culture such as described in Kohler et al. (1975) Nature 256, 495 and U.S. Pat. No. 4,376,110; the human B-cell hybridoma technique (Kosbor et al. (1983) Immunol Today 4, 72; Cole et al. (1983) Proc. Natl. Acad. Sci. USA 80, 2026, and the EBV-hybridoma technique (Cole et al. (1983) Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies disclosed herein may be cultivated in vitro or in vivo. The ability to produce high titers of monoclonal antibodies in vivo makes it a particularly useful method of production.

After obtaining antibodies specific to IL-17RB, their ability to neutralize IL-17RB can be determined by a routine procedure. Antigen-binding fragments of the just-mentioned IL-17RB neutralizing antibody can be prepared via routine methods. For example, F(ab')2 fragments can be produced by pepsin digestion of an antibody molecule, and Fab fragments that can be generated by reducing the disulfide bridges of F(ab')2 fragments.

The IL-17RB neutralizing antibody can also be used as a basis for preparing genetically engineered antibodies, including chimeric antibody, humanized antibody, and single-chain antibody. Techniques developed for the production of "chimeric antibodies" can be used. See, e.g., Morrison et al. (1984) Proc. Natl. Acad. Sci. USA 81, 6851; Neuberger et al. (1984) Nature 312, 604; and Takeda et al. (1984) Nature 314:452. A chimeric antibody is a molecule in which different portions are derived from different animal species, such as those having a variable region derived from a murine monoclonal antibody and a human immunoglobulin constant region. Antibodies can also be humanized by methods known in the art. For example, monoclonal antibodies with a desired binding specificity can be commercially humanized.

Fully human antibodies, such as those expressed in transgenic animals are also features of this disclosure (see, e.g., Green et al. (1994) Nature Genetics 7, 13; and U.S. Pat. Nos. 5,545,806 and 5,569,825). Alternatively, fully human antibodies can be obtained by screening a human antibody library (e.g., a phage display or yeast display library) against an antigen (e.g., IL-20R1).

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage scFv library and scFv clones specific to IL-17RB can be identified from the library following routine procedures. Positive clones can be subjected to further screening to identify those that suppress IL-17RB activity.

Antibodies of the present invention, or fragments thereof, may possess any of a variety of biological or functional characteristics. In certain embodiments, these antibodies are IL-17RB oprotein specific antibodies, indicating that they specifically bind to or preferentially bind to IL-17RB in a cell.

In particular embodiments, an antibody of the present invention is an antagonist antibody, which partially or fully blocks or inhibits a biological activity of a polypeptide or cell to which it specifically or preferentially binds. In other embodiments, an antibody of the present invention is a growth inhibitory antibody, which partially or fully blocks or inhibits the growth of an infected cell to which it binds. In another embodiment, an antibody of the present invention induces apoptosis. In yet another embodiment, an antibody of the present invention induces or promotes antibody-dependent cell-mediated cytotoxicity or complement dependent cytotoxicity.

Identified human antibodies may then be characterized further. For example the particular conformational epitopes within the IL-17RB polypeptides that are necessary or sufficient for binding of the antibody may be determined, e.g., using site-directed mutagenesis of expressed IL-17RB polypeptides. These methods may be readily adapted to identify human antibodies that bind any protein expressed on a cell surface.

Polynucleotide sequences encoding the antibodies, variable regions thereof, or antigen-binding fragments thereof may be subcloned into expression vectors for the recombinant production of human anti-IL-17RB antibodies. In one embodiment, this is accomplished by obtaining mononuclear cells from the patient from the serum containing the identified IL-17RB antibody; producing B cell clones from the mononuclear cells; inducing the B cells to become antibody-producing plasma cells; and screening the supernatants produced by the plasma cells to determine if it contains the IL-17RB antibody. Once a B cell clone that produces an IL-17RB antibody is identified, reverse-transcription polymerase chain reaction (RT-PCR) is performed to clone the DNAs encoding the variable regions or portions thereof of the IL-17RB antibody. These sequences are then subcloned into expression vectors suitable for the recombinant production of human IL-17RB antibodies. The binding specificity may be confirmed by determining the recombinant antibody's ability to bind cells expressing IL-17RB polypeptide.

Isolated polynucleotides encoding a polypeptide of the present invention may be subcloned into an expression vector to recombinantly produce antibodies and polypeptides of the present invention, using procedures known in the art and described therein.

Binding properties of an antibody (or fragment thereof) to IL-17RB polypeptides or IL-17RB expressing cells or tissues may generally be determined and assessed using immunodetection methods including, for example, immunofluo-

Antisense Nucleic Acids

An antisense nucleic acid of IL-17RB, DNA or RNA, is an oligonucleotide capable of forming base-pairs with the IL-17RB gene (either the sense chain or the antisense chain), thereby suppressing its expression. Preferably, the oligonucleotide has a maximum length of 150 (e.g., 100, 80, 60, or 40) nucleotides.

The antisense nucleic acid can be a double-strand RNA (dsRNA) that inhibits the expression of IL-17RB via RNA interference. RNA interference (RNAi) is a process in which a dsRNA directs homologous sequence-specific degradation of messenger RNA. In mammalian cells, RNAi can be triggered by 21-nucleotide duplexes of small interfering RNA (siRNA) without activating the host interferon response. The dsRNA used in the methods disclosed herein can be a siRNA (containing two separate and complementary RNA chains) or a short hairpin RNA (shRNA chain forming a tight hairpin structure), both of which can be designed based on the sequence of the target gene. Alternatively, it can be a microRNA.

Preferably, an antisense nucleic acid as described above contains non-naturally-occurring nucleobases, sugars, or covalent internucleoside linkages (backbones). Such a modified oligonucleotide confers desirable properties such as enhanced cellular uptake, improved affinity to the target nucleic acid, and increased in vivo stability.

In one example, the antisense nucleic acid has a modified backbone, including those that retain a phosphorus atom (see, e.g., U.S. Pat. Nos. 3,687,808; 4,469,863; 5,321,131; 5,399,676; and 5,625,050) and those that do not have a phosphorus atom (see, e.g., U.S. Pat. Nos. 5,034,506; 5,166, 315; and 5,792,608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3', 5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In another example, the antisense nucleic acid used in the disclosed methods includes one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O-alkynyl, S-alkynyl, N-alkynyl, and O-alkyl-O-alkyl. In these groups, the alkyl, alkenyl and alkynyl can be substituted or unsubstituted $C_1$ to $C_{10}$ alkyl or $C_2$ to $C_{10}$ alkenyl and alkynyl. They may also include at their 2' position heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., Helv. Chim. Acta, 1995, 78, 486-504.

In yet another example, the antisense nucleic acid includes one or more modified native nucleobases (i.e., adenine, guanine, thymine, cytosine and uracil). Modified nucleobases include those described in U.S. Pat. No. 3,687, 808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain of these nucleobases are particularly useful for increasing the binding affinity of the antisense oligonucleotide to its target nucleic acid. These include 5-substituted pyrimidines, 6-azapyrimidines and N-2, N-6 and O-6 substituted purines (e.g., 2-aminopropyladenine, 5-propynyluracil and 5-propynylcytosine). See Sanghvi, et al., eds., Antisense Research and Applications, CRC Press, Boca Raton, 1993, pp. 276-278).

Any of the antisense nucleic acids can be synthesized by methods known in the art. See, e.g., Caruthers et al., 1992, Methods in Enzymology 211, 3-19, Wincott et al., 1995, Nucleic Acids Res. 23, 2677-2684, Wincott et al., 1997, Methods Mol. Bio. 74, 59, Brennan et al., 1998, Biotechnol Bioeng., 61, 33-45, and Brennan, U.S. Pat. No. 6,001,311. It can also be transcribed from an expression vector and isolated using standard techniques.

The short hairpin RNA (hereafter referred to as "shRNA") capable of inhibiting expression of IL-17B or IL-17RB of the present invention exhibits IL-17B or IL-17RB-specific RNAi action when it targets an mRNA portion of thymidylate synthase. Accordingly, the short hairpin RNA can remarkably inhibit IL-17B or IL-17RB expression. Here, when the RNAi molecule of the present invention "targets an mRNA portion," this means that the antisense strand of shRNA described in detail below can hybridize to a target mRNA portion under stringent conditions.

Stringent conditions can be determined based on the melting temperature (Tm) for nucleic acid at which a hybrid is formed in accordance with a conventional method. For instance, washing conditions that allows maintenance of hybridization comprise, for example, generally "1×SSC, 0.1% SDS, 37° C.," more strictly "0.5×SSC, 0.1% SDS, 42° C.," and further strictly "0.1×SSC, 0.1% SDS, 65° C."

The shRNA of the present invention comprises a sense strand having a nucleotide sequence of ORF encoding TS or a nucleotide sequence partially identical thereto and an antisense strand that hybridizes under stringent conditions to the sense strand. Here, the phrase "a nucleotide sequence of ORF or a nucleotide sequence partially identical thereto" means a nucleotide sequence obtained by substituting thymine with uracil in the nucleotide sequence of ORF or a nucleotide sequence partially identical thereto.

The sense strand consists of 15 to 25 nucleotides and preferably 19 nucleotides. The nucleotide sequence of the sense strand is desirably identical to the nucleotide sequence of ORF encoding IL-17RB or IL-17B. However, it may be a substantially identical (i.e., homologous) sequence. Specifically, the nucleotide sequence of a sense strand may comprise the ORF nucleotide sequence including a substitution, a deletion, an insertion, and/or an addition of 1 or a plurality of (i.e., 1 to 3) nucleotides, preferably 1 to 2 nucleotides, and more preferably 1 nucleotide.

The antisense strand has a nucleotide sequence that can hybridize to the sense strand under stringent conditions. The antisense strand may comprise a mismatch, including a substitution, a deletion, an insertion, and/or an addition of 1 to 3 nucleotides, preferably 1 or 2 nucleotides, and more preferably 1 nucleotide as long as it can hybridize under stringent conditions. Preferably, the antisense strand consists of a nucleotide sequence perfectly complementary to the sense strand.

The nucleotide sequences of a sense strand and an antisense strand can be selected based on a known nucleotide sequence encoding IL-17B or IL-17RB (Tables 1 and 2). There are a variety of known methods for selecting such nucleotide sequences. For example, an siRNA Design Support System (Takara Bio Inc.) can be used.

A sense strand and an antisense strand are linked via a linker portion. The linker portion forms a loop such that the resulting strand is folded. Accordingly, the antisense strand and the sense strand hybridize to each other, resulting in formation of a double strand. Such a linker portion contained in a shRNA molecule is not particularly limited and thus it may be a polynucleotide linker or a non-polynucleotide linker as long as it links a sense strand and an antisense strand so as to form a stem loop structure. Preferably, a polynucleotide linker is the same consisting of 2 to 22 nucleotides known in the art. Specific examples thereof are shown in Table 3.

shRNA of the present invention can have an overhang comprising at least 2 nucleotides at the 3' end. For example, such overhang consists of a sequence comprising 1 to 5 nucleotides, preferably 1 to 3 nucleotides, and more preferably 1 or 2 nucleotides. Examples of a sequence include TTT, UU, and TT. Preferably, UU is used.

According to the present invention, preferable example of shRNA is a single strand RNA consisting of the nucleotide sequence shown in SEQ ID NOS: 5-9 as shown below in Table 4.

TABLE 4

FIVE shRNA sequences:

| | |
|---|---|
| CCATTAAGGTTCTTGTGGTTT | (SEQ ID NO: 5) |
| CCATCACACAATTTGTTACTT | (SEQ ID NO: 6) |
| CCCATAATATTCCTAATGCAA | (SEQ ID NO: 7) |
| GCAGCTGTGGATGTCCAACAA | (SEQ ID NO: 8) |
| TCTTACCATTTCCATCTTCCT | (SEQ ID NO: 9) |

Pharmaceutical Compositions and Therapy

The invention further includes pharmaceutical formulations including a polypeptide, antibody, or modulator of the present invention, at a desired degree of purity, and a pharmaceutically acceptable carrier, excipient, or stabilizer (Remingion's Pharmaceutical Sciences 16th edition, Osol, A. Ed. (1980)). In certain embodiments, pharmaceutical formulations are prepared to enhance the stability of the polypeptide or antibody during storage, e.g., in the form of lyophilized formulations or aqueous solutions.

Acceptable carriers, excipients, or stabilizers are nontoxic to recipients at the dosages and concentrations employed, and include, e.g., buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as TWEEN™, PLURONICS™ or polyethylene glycol (PEG). In certain embodiments, the therapeutic formulation preferably comprises the polypeptide or antibody at a concentration of between 5-200 mg/ml, preferably between 10-100 mg/ml.

To practice a treatment disclosed herein, an effective amount of the pharmaceutical composition noted above can be administered to a subject (e.g., a human) in need of the treatment via a suitable route. A human subject who needs the treatment may be a human patient having, at risk for, or suspected of having a disorder associated with the signaling pathway mediated by IL-17RB or IL-17B. Such a patient can be identified by routine medical examination.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

In some embodiments, the agent that suppress IL-17RB or IL-17B activity is administered to a subject in need of the treatment at an amount sufficient to reduce the level of the IL-17RB or IL-17B-mediated signaling by at least 20% (e.g., 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethylormamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients.

Intramuscular preparations, e.g., a sterile formulation of a suitable soluble salt form of the antibody, can be dissolved and administered in a pharmaceutical excipient such as Water-for-Injection, 0.9% saline, or 5% glucose solution.

When an antisense nucleic acid of IL-17RB or IL-17B is used, the nucleic acid or a vector expressing it can be delivered to a subject by methods, such as that described in Akhtar et al., 1992, Trends Cell Bio. 2, 139. For example, it can be introduced into cells using liposomes, hydrogels, cyclodextrins, biodegradable nanocapsules, or bioadhesive microspheres.

Alternatively, the nucleic acid or vector can be locally delivered by direct injection or by use of an infusion pump. Other approaches include employing various transport and carrier systems, for example through the use of conjugates and biodegradable polymers.

To facilitate delivery, any of the IL-17RB or IL-17B suppressing agents can be conjugated with a chaperon agent. As used herein, "conjugated" means two entities are associated, preferably with sufficient affinity that the therapeutic benefit of the association between the two entities is realized. Conjugated includes covalent or noncovalent bonding as well as other forms of association, such as entrapment of one entity on or within the other, or of either or both entities on or within a third entity (e.g., a micelle).

The chaperon agent can be a naturally occurring substance, such as a protein (e.g., human serum albumin, low-density lipoprotein, or globulin), carbohydrate (e.g., a dextran, pullulan, chitin, chitosan, inulin, cyclodextrin or hyaluronic acid), or lipid. It can also be a recombinant or synthetic molecule, such as a synthetic polymer, e.g., a synthetic polyamino acid. Examples of polyamino acids include polylysine (PLL), poly L-aspartic acid, poly L-glutamic acid, styrene-maleic acid anhydride copolymer, poly (L-lactide-co-glycolied) copolymer, divinyl ether-maleic anhydride copolymer, N-(2-hydroxypropyl) methacrylamide copolymer (HMPA), polyethylene glycol (PEG), polyvinyl alcohol (PVA), polyurethane, poly(2-ethylacryllic acid), N-isopropylacrylamide polymers, and polyphosphazine.

In one example, the chaperon agent is a micelle, liposome, nanoparticle, or microsphere, in which the oligonucleotide/interfering RNA is encapsulated. Methods for preparing such a micelle, liposome, nanoparticle, or microsphere are well known in the art. See, e.g., U.S. Pat. Nos. 5,108,921; 5,354,844; 5,416,016; and 5,527,5285.

In another example, the chaperon agent serves as a substrate for attachment of one or more of a fusogenic or condensing agent.

A fusogenic agent is responsive to the local pH. For instance, upon encountering the pH within an endosome, it can cause a physical change in its immediate environment, e.g., a change in osmotic properties which disrupts or increases the permeability of the endosome membrane, thereby facilitating release of the antisense oligonucleotide into host cell's cytoplasm. A preferred fusogenic agent changes charge, e.g., becomes protonated at a pH lower than a physiological range (e.g., at pH 4.5-6.5). Fusogenic agents can be molecules containing an amino group capable of undergoing a change of charge (e.g., protonation) when exposed to a specific pH range. Such fusogenic agents include polymers having polyamino chains (e.g., polyethyleneimine) and membrane disruptive agents (e.g., mellittin). Other examples include polyhistidine, polyimidazole, polypyridine, polypropyleneimine, and a polyacetal substance (e.g., a cationic polyacetal).

A condensing agent interacts with the antisense oligonucleotide, causing it to condense (e.g., reduce the size of the oligonucleotide), thus protecting it against degradation. Preferably, the condensing agent includes a moiety (e.g., a charged moiety) that interacts with the oligonucleotide via, e.g., ionic interactions. Examples of condensing agents include polylysine, spermine, spermidine, polyamine or quarternary salt thereof, pseudopeptide-polyamine, peptidomimetic polyamine, dendrimer polyamine, arginine, amidine, protamine, cationic lipid, cationic porphyrin, and alpha helical peptide.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of cancer. Alternatively, sustained continuous release formulations of the antibodies described herein may be appropriate. Various formulations and devices for achieving sustained release are known in the art.

In one example, dosages for an antibody as described herein may be determined empirically in individuals who have been given one or more administration(s) of the antibody. Individuals are given incremental dosages of the antibody. To assess efficacy of the antibody, an indicator of the disease (e.g., cancer) can be followed according to routine practice.

Generally, for administration of any of the antibodies described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate cancer, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

For the purpose of the present disclosure, the appropriate dosage of an antibody described herein will depend on the specific antibody (or compositions thereof) employed, the type and severity of the cancer, whether the antibody is administered for preventive or therapeutic purposes, previous therapy, the patient's clinical history and response to the antibody, and the discretion of the attending physician. The administration of the antibodies described herein may be essentially continuous over a preselected period of time or may be in a series of spaced dose, e.g., either before, during, or after developing cancer.

As used herein, the term "treating" refers to the application or administration of a composition including one or more active agents to a subject, who has cancer, a symptom of cancer, or a predisposition toward cancer, with the purpose to cure, heal, alleviate, relieve, alter, remedy, ameliorate, improve, or affect cancer, a symptom associated with cancer, or the predisposition toward cancer.

Alleviating cancer includes delaying the development or progression of cancer, or reducing cancer severity. Alleviating cancer does not necessarily require curative results. As used therein, "delaying" the development of cancer means to defer, hinder, slow, retard, stabilize, and/or postpone progression of cancer. This delay can be of varying lengths of time, depending on the history of cancer and/or individuals being treated. A method that "delays" or alleviates the development of cancer, or delays the onset of cancer, is a method that reduces probability (the risk) of developing one or more symptoms of cancer in a given time frame and/or reduces extent of the symptoms in a given time frame, when compared to not using the method. Such comparisons are typically based on clinical studies, using a number of subjects sufficient to give a statistically significant result.

"Development" or "progression" of cancer means initial manifestations and/or ensuing progression of cancer. Development of cancer can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of cancer includes initial onset and/or recurrence.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethylformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

Breast Cancer

Figure 3:
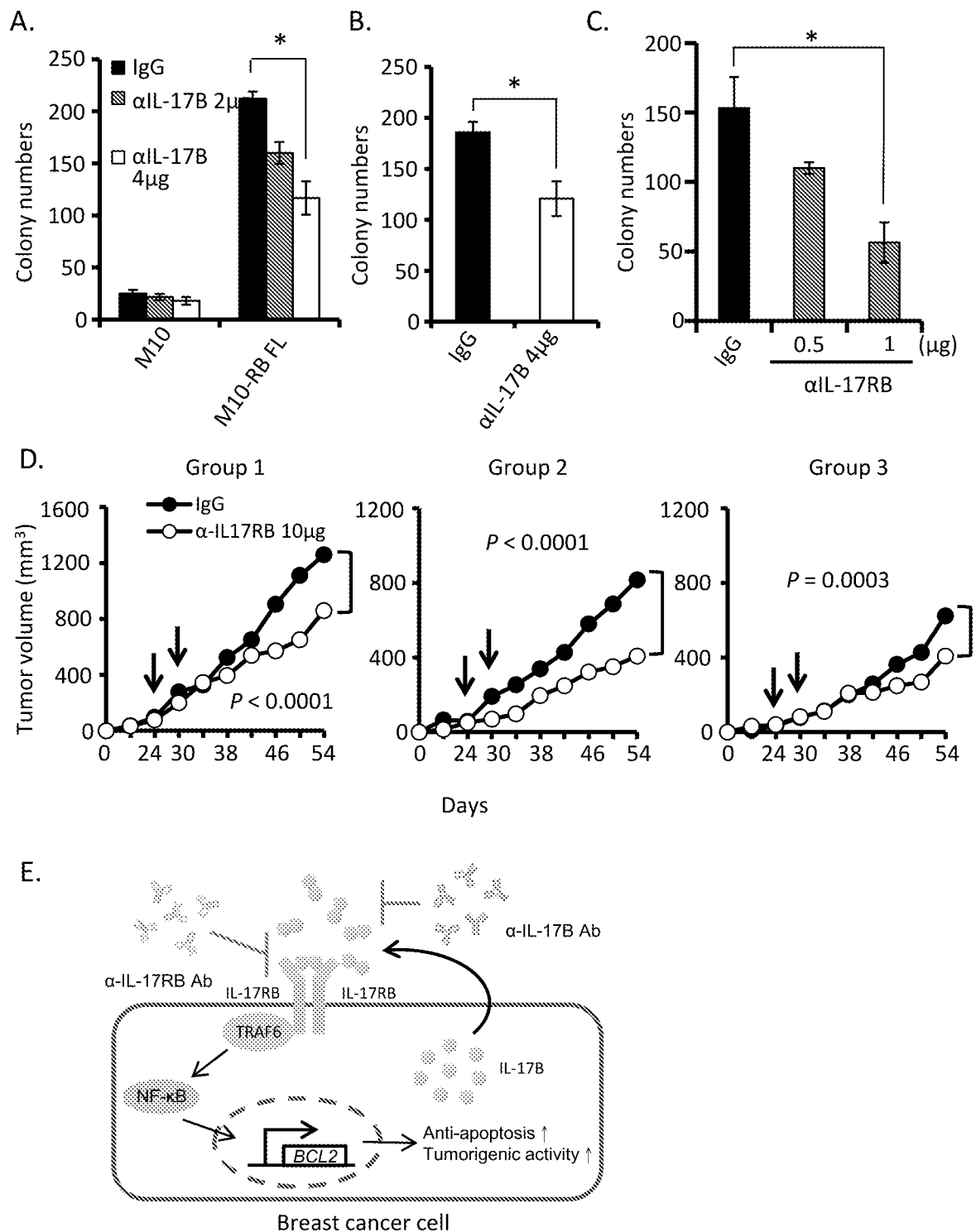
FIG. 3 shows neutralizing of IL-17RB or IL-17B with specific antibodies reduced the tumorigenicity of breast cancer cells. (A) Neutralization of IL-17B by addition of 2 and 4 µg/ml anti-IL17B antibody decreased the colony numbers of IL-17RB overexpressing M10 cells. IgG was used as a control. (B) IL-17B neutralization by addition of 4 µg/ml anti-IL17B antibody significantly decreased the colony formation of MDA-MB-361 cells. (C) Antibodies against IL-17RB (0.5 and 1 µg/ml) decreased colony numbers of MDA-MB-361 cells. (D) MDA-MB-361-derived tumors were treated with mouse normal IgG or IL-17RB antibodies by intratumoral injection. Arrows indicate the days of antibody injection. (E) Schematic shows the IL-17RB/IL-17B signaling in breast cancer cells. Targeting soluble IL-17B (blue antibodies) or the receptor IL-17RB (green antibodies) using specific antibodies is a potential therapeutic strategy to for IL-17RB associated breast cancer.

This disclosure demonstrates that amplified IL-17RB and/or IL-17B (IL-17RB/IL-17B) autocrine signaling promoted tumorigenesis in breast cancer cells. IL-17RB/IL-17B transduced signal through TRAF6 to activate NF-κB, which in turn upregulated the expression of anti-apoptotic gene Bcl-2 resulting in etoposide resistance. Blocking this pathway with either IL-17RB or IL-17B antibodies reduced breast cancer tumorigenicity (FIG. 3E). These results suggest that IL-17RB/IL-17B signal has an important role in breast tumorigenesis and may serve as a potential therapeutic target for IL-17RB expressing breast cancer.

Interleukins are known to promote malignant cell transformation and metastasis through eliciting inflammatory microenvironments. IL-17 (IL-17A) has been shown to promote tumor development through the induction of suitable microenvironments at tumor sites and myeloid-derived suppressor cells. Consistently, loss of IL-17A in mice is associated with reduced expression of Stat3-regulated cytokines and reduced tumorigenesis. Interestingly, in murine colon cancer cell-derived tumors, IL-17A has also been shown to reduce tumor growth and metastasis[28] probably through promoting cytotoxic T cell activation in tumor immunity, suggesting that ligands-receptors interaction may exert differential roles in a temporal and spatial manner. On the other hand, IL-17B appears to promote breast tumorigenesis. Although the expression of IL-17B, the cognate ligand of IL-17RB, is low in both normal and cancerous mammary epithelial cells, cancer cells overexpressing IL-17B receptor could gain their growth advantages through IL-17RB/IL-17B autocrine signal pathway.

The interaction among IL-17 ligands and receptors are intertwined. It is that the downstream signaling of IL-17RB depends greatly on the ligands and its interacting proteins. IL-17RB can transmit IL-17E signal by heterodimerization with IL-17RA. The binding of IL-17E to IL-17RB/IL-17RA induces apoptosis in breast cancer cells. In contrast, IL-17RB/IL-17B transduces the pro-survival signaling through recruitment of TRAF6 to activate NF-κB and induce anti-apoptotic process through up-regulation of Bcl-2. However, detailed molecular mechanism of how IL-17B binds to IL-17RB in a homodimer manner to transmit the signal inside the cells remains to be elucidated.

Figure 4:
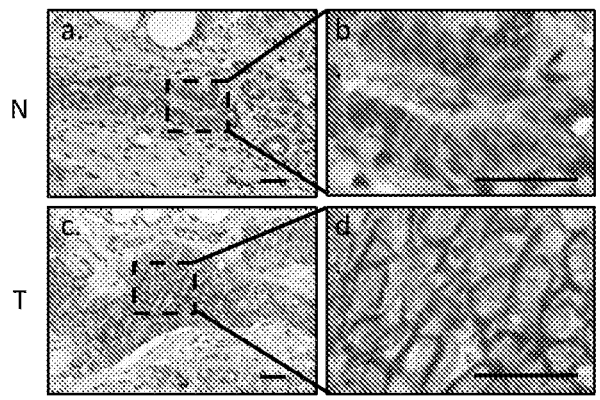
FIG. 4 shows IL-17RB overexpression was correlated with poor prognosis in breast cancer patients. (A) IHC staining of IL-17RB. The pictures showed the negative (a, b) and positive (c, d) membrane staining of IL-17RB in normal (N) and breast cancer tissue (T), respectively. (Bar, 25 µm). (B) Kaplan-Meier survival analysis of patients with IL-17RB positive and negative IHC staining. (C) Univariate and multivariate proportional hazards analysis of mortality in breast cancer patients according to IL-17RB IHC staining.
Figure 4:
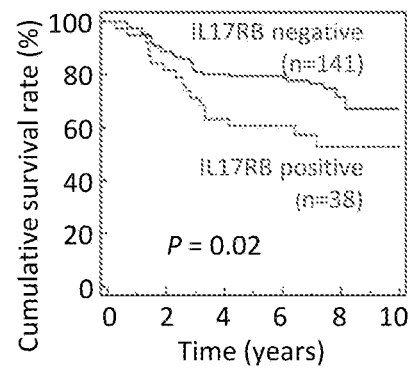

IL-17RB expression is almost undetectable in normal mammary epithelial cells. Up-regulation of this membrane receptor occurs in about 20% of breast cancer (FIG. 4). Using both Q-PCR analysis specifically detecting IL-17RB1 and IHC staining of the membrane bound IL-17RB, our data showed a significant correlation between IL-17RB1 expression and poor prognosis in breast cancer. These observations are consistent with the previous finding that IL-17RB was overexpressed in murine leukemia cells and may be oncogenic. However, Ma et al reported that the expression ratio of HOXB13/IL-17RB had a better clinical outcome in early stage ER+/lymph-node-breast cancer after receiving adjuvant tamoxifen monotherapy, implicating that overexpression of IL-17RB may be a good prognostic marker in this subset of breast cancer. Although the precise reason for this discrepancy remains to be explored, it was noted that the IL-17RB isoforms detected by Ma et al were the total IL-17RB isoforms including membrane bound and secreted, while our data indicated that only the membrane bound IL-17RB isoform 1 promotes breast tumorigenesis.

Figure 5:
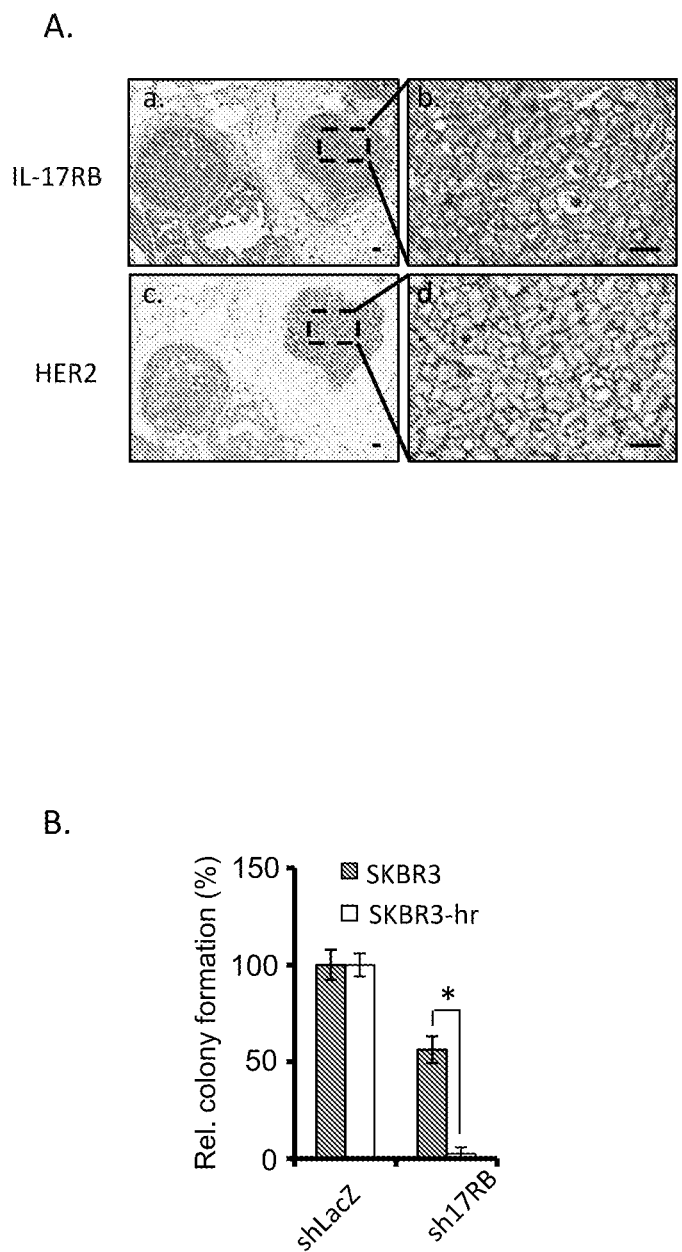
FIG. 5 shows comparison of the prognosis in breast cancer patients with elevated expression of IL-17RB or HER2. (A) IHC staining of IL-17RB (a, b) and HER2 (c, d) in serial paraffin embedded sections showed the coexistence of IL-17RB and HER2 expression. (Bar, 25 µm). (B) Depletion of IL-17RB dramatically reduced colony forming ability in trastuzumab resistant SKBR3-hr cells.

Importantly, the expression of IL-17RB was highly associated with HER2 amplification and the patients with both IL-17RB and HER2 overexpression have the shortest survival rate (FIG. 5). HER2 was overexpressed in 20-25% of breast cancers and associated with poor prognosis and drug resistance. As a EGFR tyrosine kinase, HER2, in cooperation with other receptors, transmits extrinsic signals to turn on many genes involved in proliferation and survival. Targeting HER2 with monoclonal antibody such as trastuzumab can successfully improve the prognosis; however, resistance to this treatment often occurs. Our findings that depletion of IL-17RB in trastuzumab resistant cells dramatically reduced the tumorigenic activity make IL-17RB a potential therapeutic target in HER2-positive breast cancers particularly in those resistant to trastuzumab.

Pancreatic Cancer

This disclosure demonstrates that autocrine/paracrine signaling of IL-17B/RB had an essential role in pancreatic cancer metastasis. Importantly, treating with a monoclonal antibody specifically recognizing the native form of IL-17RB successfully inhibited metastasis of IL-17RB expressing pancreatic cancers and significantly extended animal survivals.

Upregulation of chemokines in cancer cells has been attributed to constitutively activated NFκB in many cancers, including pancreatic cancer (Farrow and Evers, 2002; Rayet and Gelinas, 1999). Besides chemokines, numerous target genes of NFκB involved in promoting cell cycle activity, angiogenesis, anti-apoptosis, metastasis and tumor progression have been identified (Baldwin, 2001; Karin, 2006; Tak and Firestein, 2001; Yamamoto and Gaynor, 2001). Our finding that IL-17B/RB signaling triggered transcriptional activity of NFκB and three oncogenic transcription factors, ATF-2, AML-1 and AP-1, to cooperatively induce expression of multiple chemokines via the ERK1/2 pathway places the signaling in the key position of a multifaceted regulatory network for pancreatic cancer metastasis.

The expression of IL-17RB is independent from the entire autocrine loop feedback regulation as described here. Up-regulation of IL-17RB contributes to the major metastasis phenotypes. Thus, the amount of IL-17RB appears to be the key switcher of this entire autocrine circuit. Up-regulation of IL-17RB could be resulted from genetic and/or epigenetic events. Since genetic amplification of IL-17RB was not detected in those cancer cells with overexpression (http://www.oncomine.org), epigenetic factors and other posttranslational mechanism may mainly contribute to its up-regulation. This possibility has been under vigorous investigation. Interestingly, overexpression of several type I receptor tyrosine kinase family proteins (HER1, 2 and 3) have shown significant correlation with breast cancer malignancy (Witton et al., 2003). Whether up-regulation of other IL-17 receptor proteins may also be associated with pancreatic cancer malignancy remains to be explored.

Pancreatic cancer can only be cured at an early stage before metastasis and only if surgery can completely remove the tumor. Unfortunately, due to lack of early symptoms and the aggressive nature of pancreatic tumors, pancreatic cancer patients are often diagnosed at a late stage when metastasis has already occurred. These patients cannot be surgically treated and therefore are often subjected to chemotherapy to extend survival as long as possible. The most commonly used chemotherapy and adjuvant agents include gemcitabine, erlotinib, 5-fluorouracil (5-FU), leucovorin, irinotecan and oxaliplatin (FOLFIRINOX) (National Cancer Institute, U.S.A., http://www.cancer.gov/cancertopics/pdq/treatment/pancreatic/HealthProfessional, 12032013). Among them, gemcitabine has been approved as the first-line chemotherapeutic reagent for pancreatic cancer; but its response rate is low (10-11%) and the treatment has only a marginal effect on survival (Casper et al., 1994; Rothenberg et al., 1996). Combination therapy has also been investigated in many clinical trials to reach the best clinical outcome. However, no single agent or combination of agents has demonstrated greater clinical benefit or significantly extended median survival when compared to gemcitabine alone (Berlin et al., 2002; Burris et al., 1997; Colucci et al., 2002; Louvet et al., 2002; McKenna and Eatock, 2003; Oettle et al., 2000; Philip et al., 2001; Reni et al., 2001; Ryan et al., 2002). Since these chemotherapeutic reagents mainly target fast proliferating cells, but not block metastasis, a new adjuvant specifically targeting metastasis may be essential for effective pancreatic cancer treatment. Our findings that IL-17RB plays a critical role in pancreatic cancer malignancy, especially metastasis, and the treatment with D9 monoclonal antibody effectively prolongs diseased animal lifespan demonstrated that targeting IL-17RB may be suitable for use as an effective adjuvant treatment.

Overall, the data presented here define a novel autocrine regulatory pathway centered on IL-17B/RB in pancreatic cancer cells. IL-17B/RB signaling up-regulates at least two groups of chemokines to promote metastasis phenotype. Determining how IL-17RB is up-regulated in the pancreatic cancer cells, identifying additional downstream targets involved in metastasis, and pinpointing how IL-17B/RB participates in pancreatic cancer microenvironment remodeling allows establishment of a more complete understanding of this IL-17B/RB-centered regulatory network. Such information is used to further develop therapeutic strategies for treating pancreatic cancers.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1: High Expression of IL-17RB Promotes Breast Tumorigenesis

Depletion of IL-17RB by its corresponding shRNA in highly expressing IL-17RB cell line, MDA-MB-361, resulted in a significant decrease in soft-agar colony formation (FIG. 1A). IL-17RB depletion also significantly retarded tumor growth in a xenograft model using NOD/SCID/$\gamma^{null}$ mice (FIG. 1B). Palpable tumors derived from the control (shLacZ) and IL-17RB depleted cells (sh17RB) were both observed in the first week. However, from Day 20 to 36, tumors from control cells grew faster and larger than those from IL-17RB depleted cells. The wet weights of the tumors derived from IL-17RB depleted cells were only 40% of those from the control cells, indicating that high expression of IL-17RB promotes tumor growth.

Example 2: IL-17B Enhances Tumorigenic Activity Through IL-17RB

IL-17B, the ligand of IL-17RB, was expressed in both normal and tumor cells by RT-PCR; however, the level of the secreted ligand was barely detectable by ELISA. To test whether ectopic addition of IL-17B enhances tumorigenic activity of breast cancer cells, we generated recombinant IL-17B (rIL-17B) protein from mammalian cell expressing system. Supplement with rIL-17B increased the colony formation of MDA-MB-361 cells, which express high endogenous IL-17RB, in a dose-dependent manner. On the other hand, rIL-17B treatment failed to enhance colony formation of MDA-MB-231 cells, which express low level of IL-17RB. Similar results were also observed in M10 cells expressing IL-17RB-FL, but not the control. In contrast, depletion of the endogenous IL-17B in MDA-MB-361 cells not only inhibited the colony formation (FIG. 3A) but also decreased the NF-κB reporter activity (FIG. 3B) and Bcl2 expression. Consistently, the tumor size and weight were both reduced in IL-17B knockdown cells compared to shLacZ control in the xenograft model (FIGS. 3C and 3D). These findings suggested that IL-17B contributes to breast tumorigenesis specifically via IL-17RB.

Example 3: Antibodies Targeting to IL-17RB/IL-17B Inhibit Tumorigenicity of Breast Cancer Cells Expressing IL-17RB To further assess the importance of the IL-17RB/IL-17B signaling, we used antibodies specific to IL-17RB and IL-17B to exam their biological consequences. Addition of IL-17B antibodies to the M10 cells expressing IL-17RB or MDA-MB-361 cells inhibited their colony forming activity (FIGS. 3A and 3B). Similarly, addition of IL-17RB antibody inhibited colony formation of MDA-MB-361 cells (FIG. 3C). Importantly, the colony formation ability of MDA-MB-231 cells, which expressed little or none IL-17RB, was not affected by treating neither IL-17B nor IL-17RB antibodies. Furthermore, treatment with IL-17RB antibodies retarded tumor growth of MDA-MB-361 cells in the xenograft model (FIG. 3D). These results suggested that disruption of IL-17RB/IL-17B signaling inhibits breast tumorigenicity and use of the specific antibodies may provide a potential therapeutic strategy to treat IL-17RB positive breast cancer (FIG. 3E).

Example 4: Identification of the IL-17RB Positive Breast Cancer Specimens

The mouse monoclonal antibody A81 generated through immunogenic protein, recombinant IL-17RB extracellular domain, was used to identify the IL-17RB positive breast cancer specimens (FIG. 4A).

Example 5: Elevated IL-17RB Expression has a Stronger Correlation with Poor Prognosis than HER2 Positive Breast Cancer In a cohort with limited number of patients (69 patients), it was shown that the elevated expression of IL17RB is correlated with poor prognosis. To affirm this previous observation, an independent larger cohort of 179 breast cancer patients was further examined by immunohistochemistry (IHC). Consistently, elevated IL-17RB expression was correlated with poor prognosis (FIGS. 4A and 4B, p=0.02). The correlation between IL-17RB expression and poor prognosis was statistically significant even adjusted with several clinical parameters including age, tumor size, lymph node status, and ER expression (FIG. 4C). In addition, we also performed Q-PCR to measure IL-17RB isoform 1 transcripts amount in another independent cohort of 104 clinical breast cancer specimens and used ($-\Delta Ct=-7.55$) as a cut-off value based on a ROC (Receiver operating characteristic) curve analysis to define "high or low" IL-17RB1 expression. Kaplan-Meier (KM) analysis showed that patients with high IL-17RB1 expression had a shorter survival compared to patients with low IL-17RB1 expression. The association of IL-17RB1 expression and poor prognosis was statistically significant after adjusted with age, tumor size, lymph node status, grade and ER expression. These results suggest that high expression of IL-17RB1 may serve as a poor prognosis marker for breast cancer patients.

Intriguingly, we found that IL-17RB expression was associated with HER2 amplification in breast cancer specimens. The coexistence of IL-17RB and HER2 overexpression were further affirmed by IHC in the serial paraffin embedded breast cancer tissue sections (FIG. 5A). Patients with both high IL-17RB expression and HER2 amplification had the shortest survival rate. Interestingly, when we compared the IL-17RB or HER2 positive group with the double negative group of patients, elevated expression of IL-17RB showed a stronger correlation to poor prognosis than HER2 amplification. Both of these correlations were strengthened when the triple negative patients, who have the worst prognosis, were excluded from the cohort. These findings suggest that IL-17RB may serve as an alternative target for patients that have both HER2 amplification as well as IL-17RB expression.

To address this issue, we employed a trastuzumab (a.k.a. Herceptin)-resistant breast cancer cells. Interestingly, these cells retained the expression of IL-17RB compared to parental cells. To test whether the remaining IL-17RB offer an alternative target for further treatment, we depleted IL-17RB parental SKBR3 and SKBR3-hr cells. As shown in FIG. 5B, depletion of IL-17RB in parental cells reduced its colony formation efficiency to about 50% of the control, while depletion of IL-17RB in SKBR3-hr cells drastically abolished their colony forming ability. These results suggested that IL-17RB plays an independent role from HER2 in breast carcinogenesis and targeting to IL-17RB may offer a viable approach to treat trastuzumab-resistant cells.

Example 6: IL-17RB has an Essential Role in Pancreatic Tumorigenesis and Metastasis To investigate the potential role of IL-17RB in pancreatic cancer, we first examined the protein expression of IL-17RB in a panel of human pancreatic cancer cell lines. High IL-17RB expression was detected in HPAFII, BxPC3, Capan2 and CFPAC-1 cells. In contrast, low expression was observed in HPAC, SU.86.86 and MIA-PaCa2 cells.

To evaluate the function of IL-17RB in these pancreatic cancer cells, a series of in vitro and xenograft experiments using cells with perturbed IL-17RB expression were performed. Depletion of IL-17RB in CFPAC-1 and BxPC3 cells reduced soft-agar colony formation and invasion ability. Conversely, colony formation and invasion were enhanced in SU.86.86 and HPAC cells when full-length IL-17RB was ectopically expressed. However, expression of IL-17RB lacking a ligand binding domain (ΔLBD) had no effect.

Figure 6:
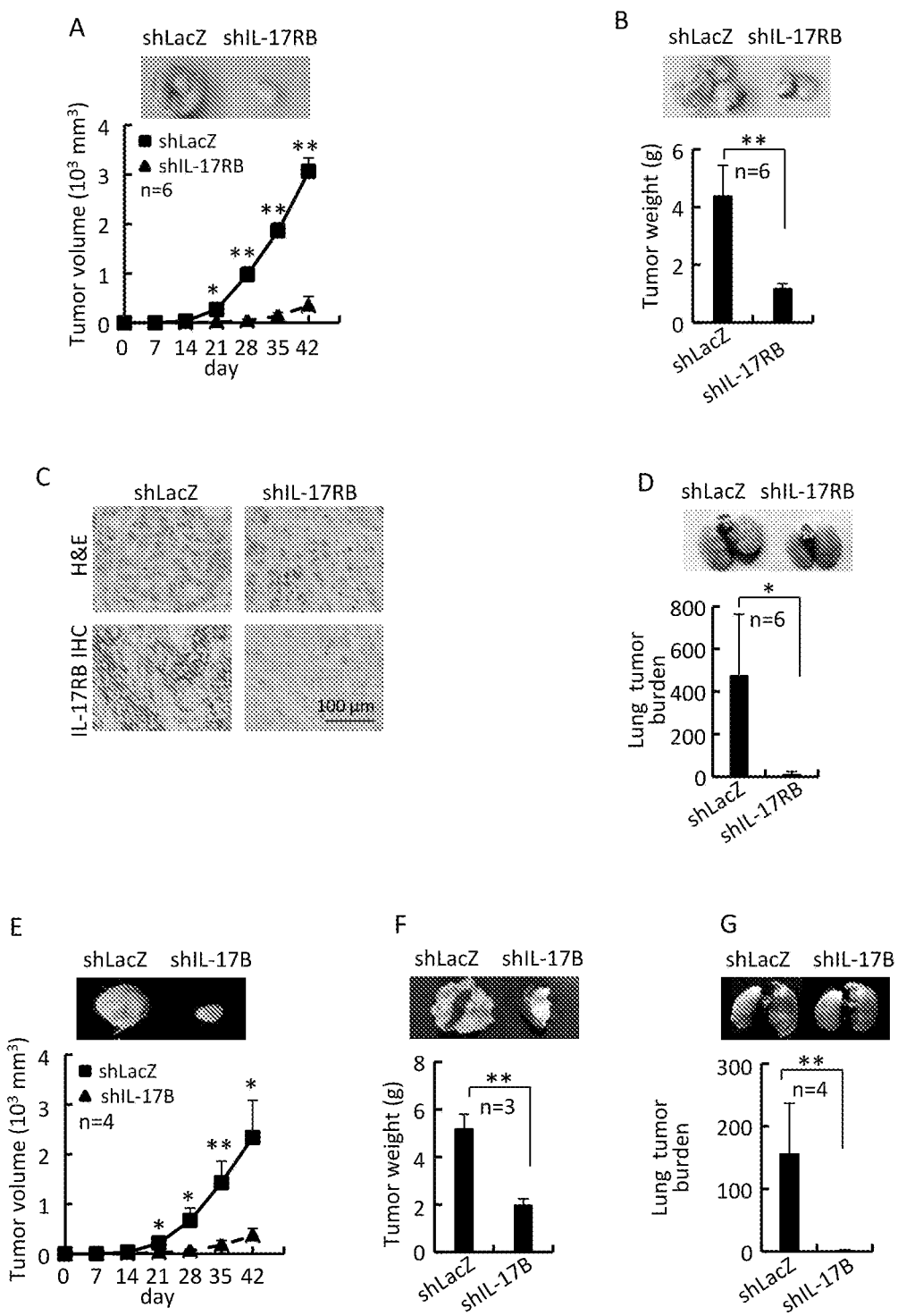
FIG. 6 shows autocrine IL-17B/RB signaling was required for pancreatic cancer tumorigenesis and metastasis. (A) Tumorigenesis assay of NOD/SCID/$\gamma^{null}$ mice subcutaneously injected with shLacZ transduced or IL-17RB depleted CFPAC-1 cells. Cell dose: 1×10$^6$ cells per mouse. Six mice were used for each group. (B) Tumor weight of NOD/SCID/$\gamma^{null}$ mice orthotopically implanted with shLacZ transduced or IL-17RB depleted CFPAC-1 cells. Cell dose: 2.5×10$^5$ cells per mouse. Six mice were used for each group. (C) IHC of IL-17RB in tumors derived from mice orthotopically implanted with shLacZ transduced or IL-17RB depleted CFPAC-1 cells. (D) Lung metastasis of NOD/SCID/$\gamma^{null}$ mice intravenously injected with shLacZ transduced or IL-17RB depleted CFPAC-1 cells. Cell dose: 2.5×10$^5$ cells per mouse. Six mice were used for each group. (E) Tumorigenesis assay of NOD/SCID/$\gamma^{null}$ mice subcutaneously injected with shLacZ transduced or IL-17B depleted CFPAC-1 cells. Cell dose: 1×10$^6$ cells per mouse. Four mice were used for each group. (F) Tumor weight of NOD/SCID/$\gamma^{null}$ mice orthotopically implanted with shLacZ transduced or IL-17B depleted CFPAC-1 cells. Cell dose: 2.5×10$^5$ cells per mouse. Three mice were used for each group. (G) Lung metastasis of NOD/SCID/$\gamma^{null}$ mice intravenously injected with shLacZ transduced or IL-17B depleted CFPAC-1 cells. Cell dose: 2.5×10$^5$ cells per mouse.

Subcutaneous xenograft assays using IL-17RB-depleted CFPAC-1 cells demonstrated that IL-17RB depletion resulted in an inhibition of tumor growth compared to the control (shLacZ) (FIG. 6A). Consistent with this, orthotopic xenografts of IL-17RB depleted CFPAC-1 cells also formed smaller tumors (FIG. 6B). IL-17RB expression in the orthotopic tumors was confirmed by immunohistochemistry (IHC) (FIG. 6C). Noticeably, four out of six mice implanted with the control CFPAC-1 cells developed lung metastasis and two of these also developed liver metastasis. In contrast, none of the IL-17RB-depleted xenograft mice developed metastasis. Consistent with the xenograft experiments, tail vein injection with IL-17RB-depleted cells led to extremely low lung metastasis while injection with control cells led to severe lung tumor burden (FIG. 6D). Similar results were observed using BxPC3 cells. Together, these data indicated that IL-17RB expression is essential for pancreatic tumor malignancy and metastasis.

Example 7: Autocrine IL-17B/RB Signaling Promotes Pancreatic Cancer Metastasis The interaction between IL-17RB and its ligand is important in promoting pancreatic tumor cell malignancy since overexpression of ΔLBD could not promote colony formation and invasion in vitro. It was found that tumor cells with high IL-17RB also expressed IL-17B, an IL-17RB ligand. Depletion of IL-17B in tumor cells abrogated colony formation and invasion in vitro, and inhibited tumor growth and metastasis in xenografted mice models (FIG. 6E-F). Inhibition of lung metastasis was further confirmed by tail-vein injection experiment (FIG. 6G). Similar results were also observed using BxPC3 cells. Thus, IL-17B overexpression also promoted tumor malignancy and metastasis.

To further evaluate the role of IL-17B/RB signaling, we treated IL-17RB expressing CFPAC-1 and BxPC3 cells with recombinant IL-17B (rIL17B). Upon addition of rIL17B, colony formation and invasion ability was further enhanced. Consistent with this, rIL17B treatment of IL-17RB overexpressing SU.86.86 and HPAC cells also increased the colony formation and invasion ability. However, rIL17B treatment could not promote either colony formation or invasion in cells overexpressing ΔLBD. These data demonstrated a critical role of autocrine IL-17B/RB signaling in malignancy of pancreatic tumor.

Figure 7:
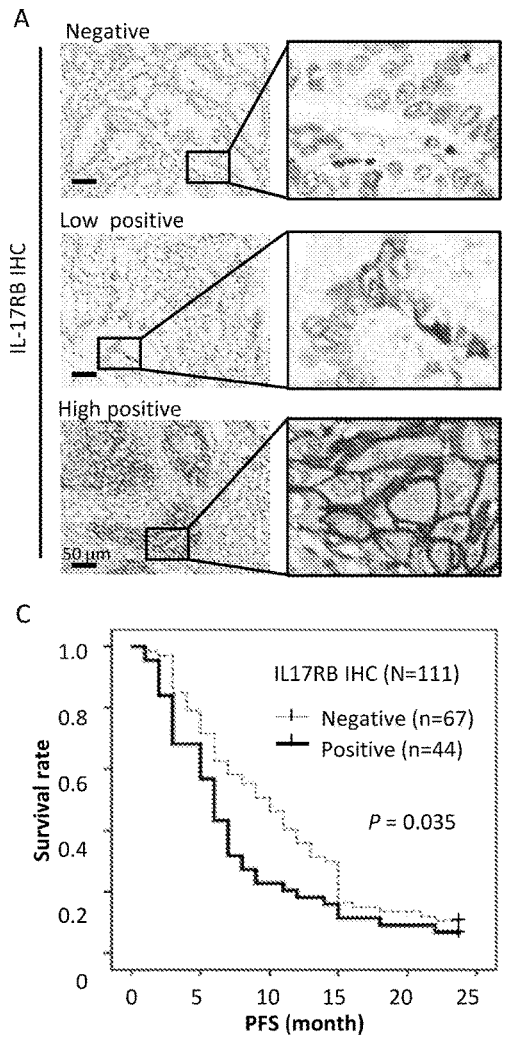
FIG. 7 shows overexpression of IL-17RB was associated with metastasis and poor clinical outcome in pancreatic cancer patients. (A) Representative pictures of the IHC analyses of IL-17RB in an IL-17RB-negative case, an IL-17RB low positive case and an IL-17RB-high case (scale bar=50 µm). Boxes show the enlarged area. (B) Correlation of IL-17RB expression and clinical parameters in 111 pancreatic cancer cases. $\chi^2$ test was used. (C) Comparison of the progression free survival (PFS) of patients with or without IL-17RB expression using the Kaplan-Meier method. (D) Univariate and multivariate Cox regression analysis of the influence of IL-17RB expression on the clinical outcome of 111 pancreatic cancer patients after surgical therapy.

Example 8: Identification of the IL-17RB Positive Pancreatic Cancer Specimens The mouse monoclonal antibody A81 generated through immunogenic protein, recombinant IL-17RB extracellular domain, was used to identify the IL-17RB positive pancreatic cancer specimens (FIG. 7A).

Example 9: Overexpression of IL-17RB Associates with Metastasis and Poor Clinical Outcome in Pancreatic Cancer Patients To further explore whether these in vitro findings were reflected in clinical outcomes, we performed IHC to analyze IL-17RB expression in 111 pancreatic cancer specimens (FIG. 7A). The specimens can be grouped into three categories based on the percentage of cells expressing IL-17RB: negative (0%), low positive (<10%) and high positive 10%). High expression of IL-17RB was positively correlated with poor differentiation (p=0.049), metastasis (p=0.009) and tumor stage using the TNM (Tumor, Node, Metastasis) staging system (p=<0.001). Moreover, high IL-17RB expression was associated with post-operative metastasis (p=0.029, FIG. 7B), marginally associated with recurrence (p=0.057, FIG. 7B) and correlated with poor prognosis (IL-17RB positive vs. negative: p=0.035, FIG. 7C; IL-17RB high positive vs. negative: p=0.007). The hazard ratio of patients with high IL-17RB expression was 1.5 fold (95% C.I.: 1.03-2.27, p=0.034) of those without detectable IL-17RB expression after adjusting for age, gender, tumor location, differentiation status, pathological type, stage and adjuvant therapy (FIG. 7D). Further, we found a significant positive correlation between IL-17RB and TFF1 expression, which served as an example of IL-17RB downstream chemokines. Together, these results all support a model whereby elevated autocrine IL-17B/RB signaling enhances tumor malignancy in pancreatic cancer. Such results suggest IL-17RB as a promising target for treatment.

Figure 8:
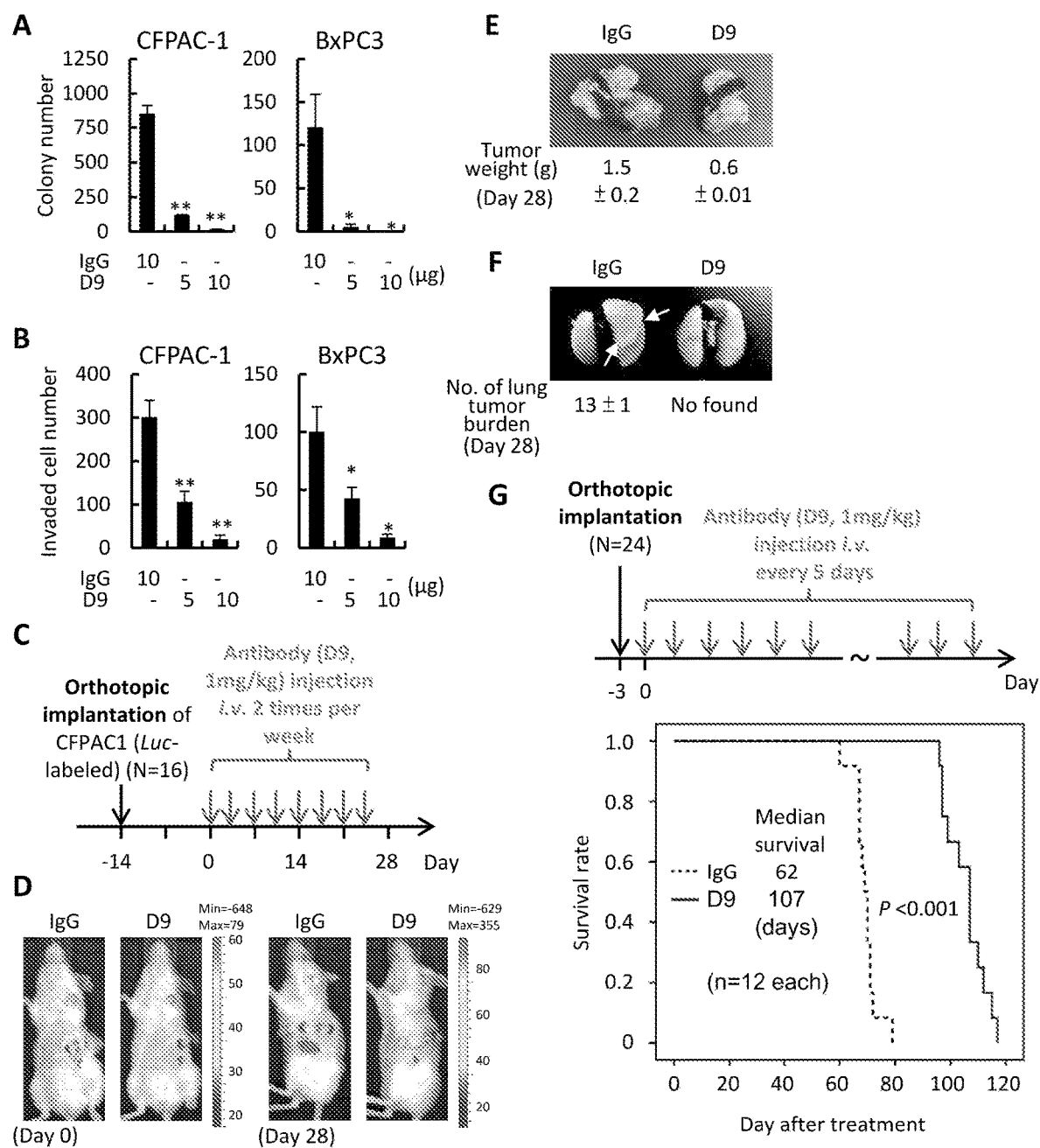
FIG. 8 shows treatment with a monoclonal anti-IL-17RB antibody (D9) blocked tumor growth, inhibited metastasis and promoted survivals. (A) Soft agar colony formation and (B) invasion assays using CFPAC-1 and BxPC3 cells treated with control IgG or D9 antibody. (C) Schematic diagram of antibody treatment in orthotopically xenografted mice. (D) IVIS image and (E) tumor weight of antibody-treated NOD/SCID/$\gamma^{null}$ mice orthotopically implanted with CFPAC-1 cells on Day 28. Cell dose: 2.5×10$^5$ cells per mouse. Eight mice were used for each group. Two mice from each group were sacrificed on Day 28 for tumor weight measurement. (F) Lung metastasis of antibody-treated NOD/SCID/$\gamma^{null}$ mice orthotopically injected with CFPAC-1 cells. Cell dose: 2.5×10$^5$ cells per mouse. Six mice were used for each group. (G) Top: Schematic diagram of antibody treatment in orthotopically xenografted mice. Bottom: Comparison of the survival periods of the antibody-treated NOD/SCID/$\gamma^{null}$ mice orthotopically injected with CFPAC-1 cells using the Kaplan-Meier method.

Example 10: Treatment with a Newly Developed Monoclonal Anti-IL-17RB Antibody Blocks Tumor Growth, Inhibits Metastasis and Promotes Survivals in a Xenografted Model To develop a useful and specific anti-IL-17RB antibody for treatment purpose, we used recombinant IL-17RB extracellular domain (amino acid 18-289). Treatment with a monoclonal antibody (D9), which recognized native IL-17RB, inhibited both colony formation and invasion ability of IL-17RB expressing pancreatic cancer cells in vitro (FIG. 8A, 8B). To test its efficacy in vivo, we orthotopically implanted luciferase-labeled CFPAC-1 cells in NOD/SCID/$\gamma^{null}$ mice, which were subjected to eight doses of D9 and control IgG treatment (20 ug per dose) intravenously (FIG. 8C). Treatment of D9 significantly reduced tumor sizes (FIG. 8D, 8E) and inhibited lung metastasis (FIG. 8F). Importantly, continuous treatment to those diseased animals with anti-IL17RB, D9, significantly extended their survival (p<0.001) by approximately 1.5 months (FIG. 8G). These results suggested that targeting IL-17RB with specific antibodies is an efficient strategy to ablate tumorigenesis and metastasis of IL-17RB expressing pancreatic cancer.

Example 11: Specificity and Binding Efficiency of Anti-IL17RB Chimeric D9 Antibody (cD9)

Figure 9:
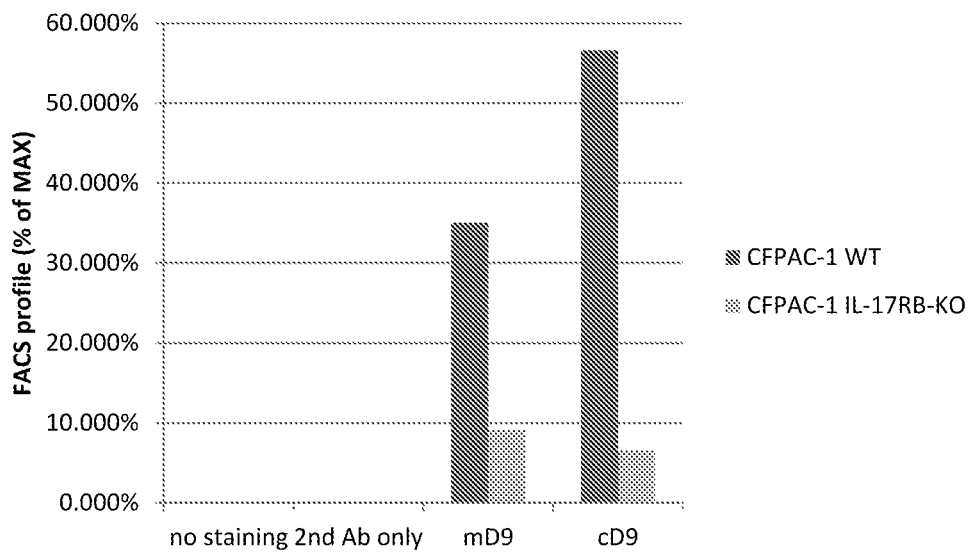
FIG. 9. Specificity and Binding Efficiency of anti-IL17RB chimeric D9 antibody (cD9). A, the specific recognition of mouse and chimeric D9 antibody to IL-17RB was determined by FACS analysis using IL-17RB expression (WT) and IL-17RB knock-out (KO) pancreatic cancer cell line CFPAC-1. The FACS profiling of no antibody (no staining) or secondary antibody only (2$^{nd}$ Ab only) were served as control. B, the recognition efficiency of mouse and chimeric D9 antibody was measured by FACS analysis using IL-17RB expression pancreatic cancer cell lines, CFPAC-1 and HPAF-II. MCF10A with no IL-17RB expression was served as negative control.
Figure 9:
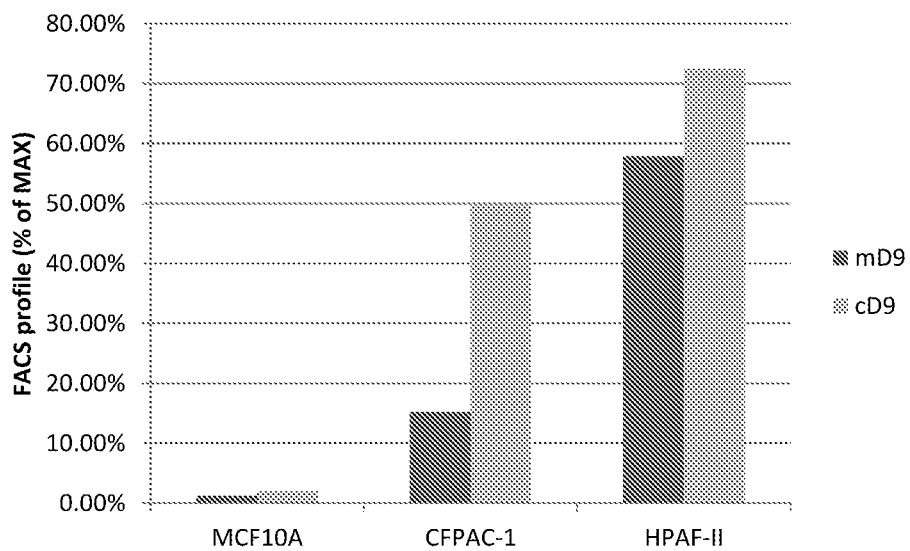

The specificity (FIG. 9A) and binding efficiency (FIG. 9B) of anti-IL17RB chimeric D9 antibody (cD9) was similar to mouse monoclonal D9 antibody (D9) using FACS analysis. These results suggest that cD9 may have the similar biological effect as mD9.

Figure 10:
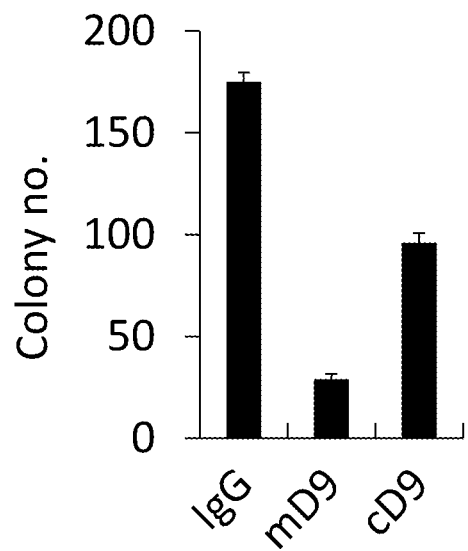
FIG. 10. Chimeric D9 antibody (cD9) inhibits tumorigenic activity of pancreatic cancer cell lines. Soft agar colony formation assay was used to evaluate the tumorigenic activity of the IL-17RB positive pancreatic cancer cells, CFPAC1 (A) and HPAF-II (B), after treating with cD9 antibody. The colony numbers generated from IgG or D9 antibody treated groups were served as negative and positive control respectively.
Figure 10:
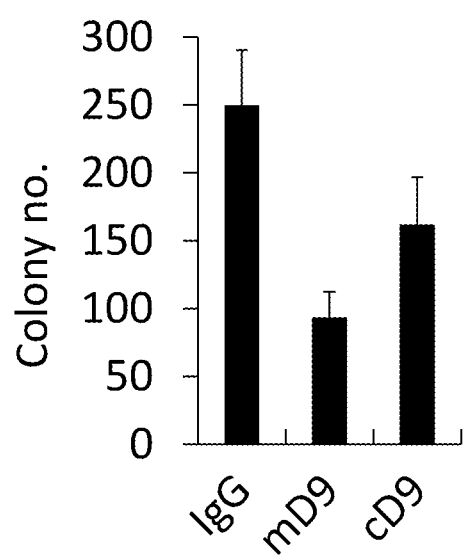

Example 12: Chimeric D9 Antibody (cD9) Targeting to IL-17RB Inhibits Tumorigenic Activity of Pancreatic Cancer Cell Lines To further assess the suppression effect to tumorigenic activity of chimeric D9 antibody (cD9) that derived from D9, the colony forming ability assay was performed. The IL-17RB expressed pancreatic cancer cells, CFPAC-1 (FIG. 10A) and HPAF-II (FIG. 10 B), were subjected to soft agar colony formation assay. Addition of cD9 can inhibit the colony number significantly in both cancer cells compared to the IgG control. The inhibition efficiency was similar to D9. These results strongly suggested that chimeric D9 antibody (cD9) provides a potential therapeutic strategy to treat IL-17RB positive cancers.

Material and Methods (Breast Cancer)

Cell Lines

Human breast cancer cell lines MDA-MB-231, MDA-MB-361, SKBR3 and SKBR3-hr were cultured in Dulbecco's modified Eagle's medium supplemented with 10% fetal bovine serum and antibiotics/antimycotics. Non-malignant mammary epithelial cell lines H184B5F5/M10 (M10) and MCF 10A cells were cultured in Minimal Essential Medium supplemented with 10% fetal bovine serum and Dulbecco's modified Eagle's medium/F12 supplemented with 5% horse serum, 20 ng/ml epidermal growth factor, 0.5 µg/ml hydrocortisone, 100 ng/ml cholera toxin, 10 µg/ml insulin and antibiotics/antimycotics in a humidified 37° C. incubator supplemented with 5% $CO_2$. H184B5F5/M10 cell line was purchased from Bioresource Collection and Research Center (BCRC) in Taiwan, and others were purchased from ATCC.

Clinical Specimens

All human samples were obtained from National Taiwan University Hospital (NTUH). The samples were encoded to protect patient confidentiality and used under protocols approved by the Institutional Review Board of Human Subjects Research Ethics Committee of Academia Sinica (AS-IRB02-98042) and NTUH, Taipei, Taiwan (#200902001R). Clinical information was obtained from pathology reports. Patients with at least 5 year follow-up were included in this study.

Soft Agar Colony Formation Assay

In one well of a 12-well plate, 2500 cells were seeded in culture medium containing 0.35% agar on top of a layer of culture medium containing 0.5% agar (M10 cells also used MCF 10A culture medium in soft colony formation assay). Cells were maintained in a humidified 37° C. incubator for 16 days and colonies were fixed with ethanol containing 0.05% crystal violet for quantification. For addition of rIL-17B protein or IL-17B/IL-17RB neutralization assays, anti-human IL-17B (R&D Systems), anti-human IL-17RB antibodies or rIL-17B was added to the soft agar culture every 2 days.

Xenograft Assay in NOD/SCID/$\gamma^{null}$ Mice

Animal care and experiments were approved by the Institutional Animal Care and Utilization Committee of Academia Sinica (IACUC #080085). $2 \times 10^6$ MDA-MB-361 breast cancer cells mixed with equal volume of Matrigel (BD bioscience) were injected into NOD/SCID/$\gamma^{null}$ fat pads. Tumor volumes were evaluated every 4 days after initial detection. Student's t-test was used to test the significant differences between shLacZ, shIL-17RB, and shIL-17B cells derived tumor growth. In vivo administration of IL-17RB antibody was initiated when tumors reached 50-100 mm$^3$, and the mice were divided into a same group with comparable tumor size. For each tumor, 10 µg of IL-17RB antibody in 20 µl sterile PBS was administrated by intratumoral injection. Non-linear regression (curve fit) was used to evaluate the statistical significance of tumor growth between control and treated mice in each group.

IL-17RB Polyclonal Antibodies

Recombinant IL-17RB extracellular domain was generated by ectopic overexpression in HEK293 cells. Polyclonal antibody generated through this immunogen was used throughout the entire work.

Immunohistochemistry

Formalin-fixed paraffin embedded primary tumor tissue sections were used. Antigen retrieval was performed using EDTA buffer (Trilogy) heated for 10 min in a microwave. Endogenous peroxidase activity was eliminated by 3% $H_2O_2$. The slides were blocked in PBS containing 10% FBS and then incubated with purified mouse anti-IL17RB polyclonal antibody (1:100) or anti-HER2 rabbit antibody (1:100) overnight at 4° C. HRP conjugated rabbit/mouse polymer (Dako REAL EnVision) and liquid diaminobenzidine tetrahydrochloride plus substrate (DAB chromogen) were used for visualization. All slides were counterstained with hematoxylin, and the images were taken using an Aperio Digital Pathology System. Samples were identified as IL-17RB positive if more than 5% of the tumor cells were positive for membrane staining.

NF-κB Reporter Assay

Cells of 80% confluence were transfected using Lipofectamine 2000 (Invitrogen). For NF-κB reporter assay, 0.5 µg NF-κB luciferase reporter plasmid and 50 ng of the pGL4-74 *Renilla* luciferase plasmid (as a transfection efficiency control) were co-transfected into cells per well (24-well plate). Cell extracts were prepared at 24 h after transfection, and the luciferase activity was measured using the Dual-Glo Luciferase Assay System (Promega) following the manufacturer's instruction.

Materials and Methods (Pancreatic Cancer)

Cell Culture

Human pancreatic cancer cell lines BxPC-3 and CFPAC-1 cells were obtained from ATCC and cultured in ATCC suggested complete growth medium in a humidified 37° C. incubator supplemented with 5% $CO_2$.

Soft Agar Colony Formation Assay

Soft agar colony formation assay was performed as previously described (Hwang-Verslues et al., 2009). In brief, 2500 cells were seeded in a layer of 0.35% agar/complete growth medium over a layer of 0.5% agar/complete growth medium in a well of a 12-well plate. Additional 50 µl of serum-free media containing 50 ng rIL17B or 1 µg anti-IL-17RB antibody was added weekly. On day 14 or 28, after seeding, crystal violet-stained colonies were counted.

IL-17RB Monoclonal Antibody

Recombinant IL-17RB extracellular domain was generated by ectopic overexpression in HEK293 cells. Monoclonal antibodies A81 and D9 generated through this immunogen displayed high specificity against endogenous IL-17RB.

Generation of Chimeric Monoclonal Antibody D9 (cD9)

The cDNA of the variable regions of D9 were cloned into IG vectors of human Fc (cD9 plasmid). The chimeric antibody was produced from cD9 plasmid DNA transfected Expi293F cells.

FACS Analysis

Cells were incubated with anti-IL-17RB mouse monoclonal antibody and Alexa 488 conjugated anti-mouse antibody for 30 mins at 4° C. The Alexa 488 positive cells were analyzed by a FACS Canto cell sorter (BD Bioscience, San Jose, Calif., USA).

Immunohistochemistry (IHC)

Formalin-fixed paraffin embedded primary tumor tissue sections were used for IHC. Heat induced antigen retrieval was performed using 0.1M citrate buffer, pH 6.0 and autoclaved for 20 min. Endogenous peroxidase was eliminated with 3% $H_2O_2$. Slides were blocked with a homemade anti-IL-17RB antibody in PBS/10% FBS and anti-TFF1 antibody (1:100, EPR3972, Genetex) or anti-CD31 rabbit polyclonal antibody (1:50, GTX81432) in PBS/5% FBS overnight at 4° C. After washing, slides were incubated with HRP rabbit/mouse polymer before visualization with liquid diaminobenzidine tetrahydrochloride plus substrate DAB chromogen from Dako REAL EnVision (Carpinteria, Calif.). All slides were counterstained with hematoxylin. The images were captured by an Aperio Digital Pathology system. For $CD31^+$ endothelial cell counting, four fields from each section of four sections were used.

Mouse Tumorigenicity and Metastasis Assays

Animal care and experiments were approved by the Institutional Animal Care and Utilization Committee of Academia Sinica (IACUC #10-04-065). IVIS kinetics imaging system (Caliper LifeSciences) was used to monitor tumor growth and metastasis. For tumorigenicity assay, non-obese diabetic/severe combined immunodeficient (NOD/SCID/$\gamma^{null}$) were injected with $2.5 \times 10^5$ GFP-LUC-tagged CFPAC-1 cells orthotopically. For subcutaneous implantation, $1 \times 10^6$ GFP-LUC-tagged CFPAC-1 cells were injected. Tumor volumes were evaluated every 7 days. Mice were sacrificed 56 days after orthotopic implantation or 42 days after subcutaneous injection. The tumors were weighed for tumorigenesis evaluation and liver and lung were examined for metastatic cancer cells. For in vivo metastasis assay, $5 \times 10^5$ GFP-LUC-tagged CFPAC-1 cells were injected intravenously. The lungs were inspected for tumor burden 70 days after injection.

Statistical Analysis

Except for the clinical correlation and quantification for specific immunoblots, all data are presented as means±SD, and Student's t-test was used to compare control and treatment groups. Asterisk (*) and (**) indicate statistical significance with p-value <0.05 and <0.01, respectively. The following analyses were performed using SPSS statistics software: A Chi-square ($\chi^2$) test was used to examine the correlation between IL-17RB expression and the clinical parameters in 111 pancreatic cancer cases. The Kaplan-Meier estimation method was used for overall progression free survival analysis, and a log-rank test was used to compare differences. Univariate and multivariate Cox regression analyses were performed to evaluate the influence of IL-17RB expression on the clinical outcome of pancreatic cancer patients after surgery.

REFERENCES

Zhu X, Mulcahy L A, Mohammed R A, Lee A H, Franks H A, Kilpatrick L, et al. IL-17 expression by breast-cancer-associated macrophages: IL-17 promotes invasiveness of breast cancer cell lines. *Breast Cancer Res* 2008; 10: R95.

Wang L, Yi T, Kortylewski M, Pardoll D M, Zeng D, Yu H. IL-17 can promote tumor growth through an IL-6-Stat3 signaling pathway. *J Exp Med* 2009; 206: 1457-1464.

Furuta S, Jeng Y M, Zhou L, Huang L, Kuhn I, Bissell M J, et al. IL-25 Causes Apoptosis of IL-25R-Expressing Breast Cancer Cells Without Toxicity to Nonmalignant Cells. *Sci Transl Med* 2011; 3: 78ra31.

Rickel E A, Siegel L A, Yoon B R, Rottman J B, Kugler D G, Swart D A, et al. Identification of functional roles for both IL-17RB and IL-17RA in mediating IL-25-induced activities. *J Immunol* 2008; 181: 4299-4310.

Acharyya, S., Oskarsson, T., Vanharanta, S., Malladi, S., Kim, J., Morris, P. G., Manova-Todorova, K., Leversha, M., Hogg, N., Seshan, V. E., et al. (2012). A CXCL1 paracrine network links cancer chemoresistance and metastasis. Cell 150, 165-178.

Arumugam, T., Brandt, W., Ramachandran, V., Moore, T. T., Wang, H., May, F. E., Westley, B. R., Hwang, R. F., and Logsdon, C. D. (2011). Trefoil factor 1 stimulates both pancreatic cancer and stellate cells and increases metastasis. Pancreas 40, 815-822.

Baldwin, A. S., Jr. (2001). Series introduction: the transcription factor N F-kappaB and human disease. The Journal of clinical investigation 107, 3-6.

Berlin, J. D., Catalano, P., Thomas, J. P., Kugler, J. W., Haller, D. G., and Benson, A. B., 3rd (2002). Phase III study of gemcitabine in combination with fluorouracil versus gemcitabine alone in patients with advanced pancreatic carcinoma: Eastern Cooperative Oncology Group Trial E2297. Journal of clinical oncology: official journal of the American Society of Clinical Oncology 20, 3270-3275.

Burris, H. A., 3rd, Moore, M. J., Andersen, J., Green, M. R., Rothenberg, M. L., Modiano, M. R., Cripps, M. C., Portenoy, R. K., Storniolo, A. M., Tarassoff, P., et al. (1997). Improvements in survival and clinical benefit with gemcitabine as first-line therapy for patients with advanced pancreas cancer: a randomized trial. Journal of clinical oncology: official journal of the American Society of Clinical Oncology 15, 2403-2413.

Campbell, A. S., Albo, D., Kimsey, T. F., White, S. L., and Wang, T. N. (2005). Macrophage inflammatory protein-3alpha promotes pancreatic cancer cell invasion. The Journal of surgical research 123, 96-101.

Casper, E. S., Green, M. R., Kelsen, D. P., Heelan, R. T., Brown, T. D., Flombaum, C. D., Trochanowski, B., and Tarassoff, P. G. (1994). Phase II trial of gemcitabine (2,2'-difluorodeoxycytidine) in patients with adenocarcinoma of the pancreas. Investigational new drugs 12, 29-34.

Clark, C. E., Hingorani, S. R., Mick, R., Combs, C., Tuveson, D. A., and Vonderheide, R. H. (2007). Dynamics of the immune reaction to pancreatic cancer from inception to invasion. Cancer research 67, 9518-9527.

Colucci, G., Giuliani, F., Gebbia, V., Biglietto, M., Rabitti, P., Uomo, G., Cigolari, S., Testa, A., Maiello, E., and Lopez, M. (2002). Gemcitabine alone or with cisplatin for the treatment of patients with locally advanced and/or metastatic pancreatic carcinoma: a prospective, randomized phase III study of the Gruppo Oncologia dell'Italia Meridionale. Cancer 94, 902-910.

Farrow, B., and Evers, B. M. (2002). Inflammation and the development of pancreatic cancer. Surgical oncology 10, 153-169.

Fernando, R. I., Castillo, M. D., Litzinger, M., Hamilton, D. H., and Palena, C. (2011). IL-8 signaling plays a critical role in the epithelial-mesenchymal transition of human carcinoma cells. Cancer research 71, 5296-5306.

Frick, V. O., Rubie, C., Wagner, M., Graeber, S., Grimm, H., Kopp, B., Rau, B. M., and Schilling, M. K. (2008). Enhanced ENA-78 and IL-8 expression in patients with malignant pancreatic diseases. Pancreatology 8, 488-497.

Hong, S. M., Park, J. Y., Hruban, R. H., and Goggins, M. (2011). Molecular signatures of pancreatic cancer. Archives of pathology & laboratory medicine 135, 716-727.

Huang, C. K., Yang, C. Y., Jeng, Y. M., Chen, C. L., Wu, H. H., Chang, Y. C., Ma, C., Kuo, W. H., Chang, K. J., Shew, J. Y., and Lee, W. H. (2013). Autocrine/paracrine mechanism of interleukin-17B receptor promotes breast tumorigenesis through NF-kappaB-mediated antiapoptotic pathway. Oncogene.

Jones, S., Zhang, X., Parsons, D. W., Lin, J. C., Leary, R. J., Angenendt, P., Mankoo, P., Carter, H., Kamiyama, H., Jimeno, A., et al. (2008). Core signaling pathways in human pancreatic cancers revealed by global genomic analyses. Science 321, 1801-1806.

Karin, M. (2006). NF-kappaB and cancer: mechanisms and targets. Molecular carcinogenesis 45, 355-361.

Kleeff, J., Kusama, T., Rossi, D. L., Ishiwata, T., Maruyama, H., Friess, H., Buchler, M. W., Zlotnik, A., and Korc, M. (1999). Detection and localization of Mip-3alpha/LARC/Exodus, a macrophage proinflammatory chemokine, and its CCR6 receptor in human pancreatic cancer. International journal of cancer Journal international du cancer 81, 650-657.

Laheru, D., and Jaffee, E. M. (2005). Immunotherapy for pancreatic cancer—science driving clinical progress. Nature reviews Cancer 5, 459-467.

Le, X., Shi, Q., Wang, B., Xiong, Q., Qian, C., Peng, Z., Li, X. C., Tang, H., Abbruzzese, J. L., and Xie, K. (2000). Molecular regulation of constitutive expression of interleukin-8 in human pancreatic adenocarcinoma. Journal of interferon & cytokine research: the official journal of the International Society for Interferon and Cytokine Research 20, 935-946.

Li, S., Huang, S., and Peng, S. B. (2005). Overexpression of G protein-coupled receptors in cancer cells: involvement in tumor progression. International journal of oncology 27, 1329-1339.

Lonardo, E., Frias-Aldeguer, J., Hermann, P. C., and Heeschen, C. (2012). Pancreatic stellate cells form a niche for cancer stem cells and promote their self-renewal and invasiveness. Cell Cycle 11, 1282-1290.

Lopez-Bergami, P., Lau, E., and Ronai, Z. (2010). Emerging roles of ATF2 and the dynamic AP1 network in cancer. Nature reviews Cancer 10, 65-76.

Louvet, C., Andre, T., Lledo, G., Hammel, P., Bleiberg, H., Bouleuc, C., Gamelin, E., Flesch, M., Cvitkovic, E., and de Gramont, A. (2002). Gemcitabine combined with oxaliplatin in advanced pancreatic adenocarcinoma: final results of a GERCOR multicenter phase II study. Journal of clinical oncology: official journal of the American Society of Clinical Oncology 20, 1512-1518.

Maezawa, Y., Nakajima, H., Suzuki, K., Tamachi, T., Ikeda, K., Inoue, J., Saito, Y., and Iwamoto, I. (2006). Involvement of TNF receptor-associated factor 6 in IL-25 receptor signaling. J Immunol 176, 1013-1018.

Matsuo, Y., Ochi, N., Sawai, H., Yasuda, A., Takahashi, H., Funahashi, H., Takeyama, H., Tong, Z., and Guha, S. (2009). CXCL8/IL-8 and CXCL12/SDF-1alpha co-operatively promote invasiveness and angiogenesis in pancreatic cancer. International journal of cancer Journal international du cancer 124, 853-861.

McCawley, L. J., and Matrisian, L. M. (2001). Tumor progression: defining the soil round the tumor seed. Current biology: CB 11, R25-27.

McKenna, S., and Eatock, M. (2003). The medical management of pancreatic cancer: a review. The oncologist 8, 149-160.

Menghini, R., Marchetti, V., Cardellini, M., Hribal, M. L., Mauriello, A., Lauro, D., Sbraccia, P., Lauro, R., and Federici, M. (2005). Phosphorylation of GATA2 by Akt increases adipose tissue differentiation and reduces adipose tissue-related inflammation: a novel pathway linking obesity to atherosclerosis. Circulation 111, 1946-1953.

Messeguer, X., Escudero, R., Farre, D., Nunez, O., Martinez, J., and Alba, M. M. (2002). PROMO: detection of known transcription regulatory elements using species-tailored searches. Bioinformatics 18, 333-334.

Mori, T., Doi, R., Koizumi, M., Toyoda, E., Ito, D., Kami, K., Masui, T., Fujimoto, K., Tamamura, H., Hiramatsu, K., et al. (2004). CXCR4 antagonist inhibits stromal cell-derived factor 1-induced migration and invasion of human pancreatic cancer. Molecular cancer therapeutics 3, 29-37.

Moseley, T. A., Haudenschild, D. R., Rose, L., and Reddi, A. H. (2003). Interleukin-17 family and IL-17 receptors. Cytokine & growth factor reviews 14, 155-174.

Niedergethmann, M., Alves, F., Neff, J. K., Heidrich, B., Aramin, N., Li, L., Pilarsky, C., Grutzmann, R., Allgayer, H., Post, S., and Gretz, N. (2007). Gene expression profiling of liver metastases and tumour invasion in pancreatic cancer using an orthotopic SCID mouse model. British journal of cancer 97, 1432-1440.

Oettle, H., Arning, M., Pelzer, U., Arnold, D., Stroszczynski, C., Langrehr, J., Reitzig, P., Kindler, M., Herrenberger, J., Musch, R., et al. (2000). A phase II trial of gemcitabine in combination with 5-fluorouracil (24-hour) and folinic acid in patients with chemonaive advanced pancreatic cancer. Annals of oncology: official journal of the European Society for Medical Oncology/ESMO 11, 1267-1272.

Philip, P. A., Zalupski, M. M., Vaitkevicius, V. K., Arlauskas, P., Chaplen, R., Heilbrun, L. K., Adsay, V., Weaver, D., and Shields, A. F. (2001). Phase II study of gemcitabine and cisplatin in the treatment of patients with advanced pancreatic carcinoma. Cancer 92, 569-577.

Raman, D., Baugher, P. J., Thu, Y. M., and Richmond, A. (2007). Role of chemokines in tumor growth. Cancer letters 256, 137-165.

Rayet, B., and Gelinas, C. (1999). Aberrant rel/nfkb genes and activity in human cancer. Oncogene 18, 6938-6947.

Reeves, P. J., Callewaert, N., Contreras, R., and Khorana, H. G. (2002). Structure and function in rhodopsin: high-level expression of rhodopsin with restricted and homogeneous N-glycosylation by a tetracycline-inducible N-acetylglucosaminyltransferase I-negative HEK293S stable mammalian cell line. Proc Natl Acad Sci USA 99, 13419-13424.

Reni, M., Passoni, P., Panucci, M. G., Nicoletti, R., Galli, L., Balzano, G., Zerbi, A., Di Carlo, V., and Villa, E. (2001). Definitive results of a phase II trial of cisplatin, epirubicin, continuous-infusion fluorouracil, and gemcitabine in stage IV pancreatic adenocarcinoma. Journal of clinical oncology: official journal of the American Society of Clinical Oncology 19, 2679-2686.

Rhim, A. D., Mirek, E. T., Aiello, N. M., Maitra, A., Bailey, J. M., McAllister, F., Reichert, M., Beatty, G. L., Rustgi, A. K., Vonderheide, R. H., et al. (2012). EMT and dissemination precede pancreatic tumor formation. Cell 148, 349-361.

Rothenberg, M. L., Moore, M. J., Cripps, M. C., Andersen, J. S., Portenoy, R. K., Burris, H. A., 3rd, Green, M. R., Tarassoff, P. G., Brown, T. D., Casper, E. S., et al. (1996). A phase II trial of gemcitabine in patients with 5-FU-refractory pancreas cancer. Annals of oncology: official journal of the European Society for Medical Oncology/ESMO 7, 347-353.

Ryan, D. P., Kulke, M. H., Fuchs, C. S., Grossbard, M. L., Grossman, S. R., Morgan, J. A., Earle, C. C., Shivdasani, R., Kim, H., Mayer, R. J., and Clark, J. W. (2002). A Phase II study of gemcitabine and docetaxel in patients with metastatic pancreatic carcinoma. Cancer 94, 97-103.

Ryu, B., Jones, J., Hollingsworth, M. A., Hruban, R. H., and Kern, S. E. (2001). Invasion-specific genes in malignancy: serial analysis of gene expression comparisons of primary and passaged cancers. Cancer research 61, 1833-1838.

Sawai, H., Funahashi, H., Yamamoto, M., Okada, Y., Hayakawa, T., Tanaka, M., Takeyama, H., and Manabe, T. (2003). Interleukin-1alpha enhances integrin alpha(6)beta (1) expression and metastatic capability of human pancreatic cancer. Oncology 65, 167-173.

Shi, Q., Le, X., Wang, B., Xiong, Q., Abbruzzese, J. L., and Xie, K. (2000a). Regulation of interleukin-8 expression by cellular pH in human pancreatic adenocarcinoma cells. Journal of interferon & cytokine research: the official journal of the International Society for Interferon and Cytokine Research 20, 1023-1028.

Shi, Y., Ullrich, S. J., Zhang, J., Connolly, K., Grzegorzewski, K. J., Barber, M. C., Wang, W., Wathen, K., Hodge, V., Fisher, C. L., et al. (2000b). A novel cytokine receptor-ligand pair. Identification, molecular characterization, and in vivo immunomodulatory activity. The Journal of biological chemistry 275, 19167-19176.

Song, X., and Qian, Y. (2013). IL-17 family cytokines mediated signaling in the pathogenesis of inflammatory diseases. Cellular signalling.

Takamori, H., Oades, Z. G., Hoch, O. C., Burger, M., and Schraufstatter, I. U. (2000). Autocrine growth effect of IL-8 and GROalpha on a human pancreatic cancer cell line, Capan-1. Pancreas 21, 52-56.

Tanaka, T., Kurokawa, M., Ueki, K., Tanaka, K., Imai, Y., Mitani, K., Okazaki, K., Sagata, N., Yazaki, Y., Shibata, Y., et al. (1996). The extracellular signal-regulated kinase pathway phosphorylates AML1, an acute myeloid leukemia gene product, and potentially regulates its transactivation ability. Molecular and cellular biology 16, 3967-3979.

Whitmarsh, A. J., and Davis, R. J. (1996). Transcription factor AP-1 regulation by mitogen-activated protein kinase signal transduction pathways. J Mol Med (Berl) 74, 589-607.

Xie, K. (2001). Interleukin-8 and human cancer biology. Cytokine & growth factor reviews 12, 375-391.

Yamamoto, Y., and Gaynor, R. B. (2001). Therapeutic potential of inhibition of the NF-kappaB pathway in the treatment of inflammation and cancer. The Journal of clinical investigation 107, 135-142.

All publications and patent applications cited in this specification are herein incorporated by reference as if each individual publication or patent application was specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. An isolated antibody against interleukin-17 receptor B (IL-17RB), wherein the antibody comprises a heavy chain variable region (VH) comprising the VH CDR1-3 of SEQ ID NO:14-16, respectively; and a light chain variable region (VL) comprising the VL CDR1-3 of SEQ ID NO:17-19, respectively.

2. The isolated antibody of claim 1, wherein the antibody comprises the VH of SEQ ID NO:12, and/or the VL of SEQ ID NO: 13.

3. The isolated antibody of claim 1, wherein the antibody is a full-length antibody or an antigen-binding fragment thereof.

4. The isolated antibody of claim 3, wherein the antigen binding fragment is a Fab fragment, a F(ab')2 fragment, or a single-chain Fv fragment.

5. The isolated antibody of claim 1, wherein antibody is a humanized antibody, a chimeric antibody, a mouse antibody or a single-chain antibody.

6. A composition, comprising the antibody against interleukin-17 receptor B (IL-17RB) of claim 1.

7. The composition of claim 6, wherein the composition is a pharmaceutical composition, which further comprises a pharmaceutically acceptable adjuvant and/or carrier.

8. The composition of claim 7, which further comprises a chemotherapeutic agent.

9. A method for treating cancer in a subject, comprising administering to the subject an effective amount of the composition of claim 6.

10. The method of claim 9, wherein the cancer is selected from the group consisting of pancreatic cancer, breast cancer, colorectal cancer, liver cancer, kidney cancer, head and neck cancer, esophageal cancer, gastric cancer, biliary tract cancer, gallbladder and bile duct cancer, lung cancer, mammary cancer, ovarian cancer, cervical cancer, uterine body cancer, bladder cancer, prostate cancer, testicular tumor, osteogenic and soft-tissue sarcomas, leukemia, malignant lymphoma, multiple myeloma, skin cancer, brain tumor and plura malignant mesothelioma.

11. The method of claim 10, wherein the cancer is pancreatic cancer or breast cancer.

12. The method of claim 11, wherein the cancer is HER2 positive breast cancer or trastuzumab-resistant breast cancer.

13. An isolated nucleic acid encoding the VH and/or the VL of the antibody of claim 1.

14. A vector comprising the nucleic acid of claim 13.

* * * * *